(12) United States Patent
Burbank et al.

(10) Patent No.: US 7,354,444 B2
(45) Date of Patent: Apr. 8, 2008

(54) OCCLUSION DEVICE WITH DEPLOYABLE PADDLES FOR DETECTION AND OCCLUSION OF BLOOD VESSELS

(75) Inventors: Fred H. Burbank, Laguna Niguel, CA (US); Michael L. Jones, San Clemente, CA (US); Greig E. Altieri, Laguna Beach, CA (US); R. J. Serra, Irvine, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 434 days.

(21) Appl. No.: 10/300,116

(22) Filed: Nov. 19, 2002

(65) Prior Publication Data

US 2004/0092979 A1 May 13, 2004

Related U.S. Application Data

(63) Continuation-in-part of application No. 10/107,810, filed on Mar. 28, 2002, now Pat. No. 6,905,506.

(60) Provisional application No. 60/279,477, filed on Mar. 28, 2001.

(51) Int. Cl.
*A61B 17/08* (2006.01)
(52) U.S. Cl. .................................... 606/157
(58) Field of Classification Search ............... 606/158, 606/119, 120, 151, 157, 205; 600/454, 455
See application file for complete search history.

(56) References Cited

U.S. PATENT DOCUMENTS

| | | | |
|---|---|---|---|
| 2,400,251 A | 5/1946 | Nagel | |
| 3,209,753 A | 10/1965 | Hawkins et al. | |
| 3,403,672 A * | 10/1968 | Curtis | 600/488 |
| 3,411,505 A | 11/1968 | Nobis | |
| 3,535,067 A * | 10/1970 | Lesher et al. | 600/485 |

(Continued)

FOREIGN PATENT DOCUMENTS

DE      195 28 440 A      2/1997

(Continued)

OTHER PUBLICATIONS

International Preliminary Report of Patentability for Serial No. PCT/US04/01935, mailed Jul. 8, 2005.

(Continued)

*Primary Examiner*—Anhtuan T. Nguyen
*Assistant Examiner*—Tuan V. Nguyen

(57) ABSTRACT

Devices, systems and methods for temporarily reducing or abolishing blood flow by occluding blood vessels are provided. A blood vessel-occlusion device embodying features of the invention includes a deployable pressure-applying member with a location sensor, and an applicator. The location sensor is configured to detect a blood vessel, which may be occluded by compression from the pressure-applying member. A pressure-applying member may be released from the applicator, with blood-vessel compression maintained after release. The applicator is configured to engage a guide, such as a tenaculum, to aid in the placement and operation of the applicator. A pressure-applying member may also engage the guide. The invention finds use in, for example, treating uterine disorders and conditions which may be treated by occlusion of the uterine arteries, such as uterine fibroids, dysfunctional uterine bleeding, post-partum hemorrhage, and bleeding associated with caesarian section.

22 Claims, 11 Drawing Sheets

U.S. PATENT DOCUMENTS

| | | | |
|---|---|---|---|
| 3,777,740 | A | 12/1973 | Hokanson |
| 3,779,248 | A | 12/1973 | Karman |
| 4,120,302 | A | 10/1978 | Ziegler |
| 4,226,240 | A | 10/1980 | Walker, Jr. |
| 4,292,960 | A | 10/1981 | Paglione |
| 4,428,374 | A | 1/1984 | Auburn |
| 4,428,379 | A | 1/1984 | Robbins et al. |
| 4,509,528 | A * | 4/1985 | Sahota .................. 600/504 |
| 4,650,466 | A | 3/1987 | Luther |
| 4,757,823 | A | 7/1988 | Hofmeister et al. |
| 4,945,896 | A | 8/1990 | Gade |
| 4,991,588 | A | 2/1991 | Pflueger et al. |
| 4,994,069 | A | 2/1991 | Ritchart et al. |
| 5,037,430 | A | 8/1991 | Hasson |
| 5,037,433 | A | 8/1991 | Wilk et al. |
| 5,081,997 | A | 1/1992 | Bosley, Jr. et al. |
| 5,108,408 | A | 4/1992 | Lally |
| 5,201,314 | A | 4/1993 | Bosley et al. |
| 5,226,911 | A | 7/1993 | Chee et al. |
| 5,275,166 | A * | 1/1994 | Vaitekunas et al. ......... 600/439 |
| 5,277,181 | A * | 1/1994 | Mendelson et al. ......... 600/322 |
| 5,289,831 | A | 3/1994 | Bosley |
| 5,336,229 | A | 8/1994 | Noda |
| 5,336,231 | A | 8/1994 | Adair |
| 5,383,922 | A | 1/1995 | Zipes et al. |
| 5,427,108 | A | 6/1995 | Bollinger |
| 5,456,693 | A | 10/1995 | Conston et al. |
| 5,458,596 | A | 10/1995 | Lax et al. |
| 5,488,958 | A | 2/1996 | Topel et al. |
| 5,496,331 | A | 3/1996 | Xu et al. |
| 5,507,744 | A | 4/1996 | Tay et al. |
| 5,542,944 | A | 8/1996 | Bhatta |
| 5,549,624 | A | 8/1996 | Mirigian et al. |
| 5,549,824 | A | 8/1996 | Trumpf et al. |
| 5,556,396 | A | 9/1996 | Cohen et al. |
| 5,562,680 | A * | 10/1996 | Hasson .................. 606/119 |
| 5,570,692 | A | 11/1996 | Morinaga |
| 5,582,617 | A | 12/1996 | Klieman et al. |
| 5,588,960 | A | 12/1996 | Edwards et al. |
| 5,591,173 | A | 1/1997 | Schifano |
| 5,614,204 | A | 3/1997 | Cochrum |
| 5,658,299 | A | 8/1997 | Hart |
| 5,662,676 | A | 9/1997 | Koninckx |
| 5,662,680 | A | 9/1997 | Desai |
| 5,665,096 | A | 9/1997 | Yoon |
| 5,672,153 | A | 9/1997 | Lax et al. |
| 5,672,172 | A | 9/1997 | Zupkas |
| 5,674,243 | A | 10/1997 | Hale |
| 5,691,314 | A | 11/1997 | Hodgen |
| 5,697,937 | A * | 12/1997 | Toma .................. 606/119 |
| 5,697,942 | A | 12/1997 | Palti |
| 5,702,407 | A | 12/1997 | Kaji |
| 5,713,371 | A | 2/1998 | Sherman et al. |
| 5,713,896 | A | 2/1998 | Nardelia |
| 5,713,942 | A | 2/1998 | Stern et al. |
| 5,715,832 | A | 2/1998 | Koblish et al. |
| 5,716,389 | A | 2/1998 | Walinsky et al. |
| 5,720,743 | A | 2/1998 | Bischof et al. |
| 5,749,879 | A | 5/1998 | Middleman et al. |
| 5,759,154 | A | 6/1998 | Hoyns |
| 5,766,135 | A | 6/1998 | Terwilliger |
| 5,776,129 | A | 7/1998 | Mersch |
| 5,792,059 | A | 8/1998 | Furia et al. |
| 5,797,397 | A | 8/1998 | Rosenberg |
| 5,800,378 | A | 9/1998 | Edwards et al. |
| 5,817,022 | A | 10/1998 | Vesely |
| 5,836,906 | A | 11/1998 | Edwards |
| 5,840,033 | A | 11/1998 | Takeuchi |
| 5,895,386 | A | 4/1999 | Odell et al. |
| 5,895,395 | A | 4/1999 | Yeung |
| 5,899,861 | A | 5/1999 | Friemel et al. |
| 5,904,651 | A | 5/1999 | Swanson et al. |
| 5,910,484 | A | 6/1999 | Haupert, Jr. |
| 5,911,691 | A | 6/1999 | Mochizuki et al. |
| 5,916,173 | A | 6/1999 | Kirsner |
| 5,921,933 | A | 7/1999 | Sarkis et al. |
| 5,922,008 | A | 7/1999 | Gimpelson |
| 5,941,889 | A | 8/1999 | Cermak |
| 5,979,453 | A | 11/1999 | Savage et al. |
| 6,013,088 | A | 1/2000 | Karavidas |
| 6,015,541 | A | 1/2000 | Greff et al. |
| 6,019,724 | A | 2/2000 | Gronningsaeter et al. |
| 6,032,673 | A | 3/2000 | Savage et al. |
| 6,033,398 | A | 3/2000 | Farley et al. |
| 6,034,477 | A | 3/2000 | Peeters et al. |
| 6,035,238 | A | 3/2000 | Ingle et al. |
| 6,045,508 | A | 4/2000 | Hossack et al. |
| 6,066,139 | A | 5/2000 | Ryan et al. |
| 6,077,257 | A | 6/2000 | Edwards et al. |
| 6,080,118 | A | 6/2000 | Blythe |
| 6,096,051 | A | 8/2000 | Kortenbach et al. |
| 6,106,473 | A | 8/2000 | Violante et al. |
| 6,152,874 | A | 11/2000 | Looney et al. |
| 6,169,914 | B1 | 1/2001 | Hovland et al. |
| 6,175,751 | B1 | 1/2001 | Maizes |
| 6,210,330 | B1 | 4/2001 | Tepper |
| 6,231,515 | B1 | 5/2001 | Moore et al. |
| 6,254,601 | B1 | 7/2001 | Burbank et al. |
| 6,261,234 | B1 | 7/2001 | Lin |
| 6,280,441 | B1 | 8/2001 | Ryan |
| 6,293,954 | B1 | 9/2001 | Fogarty et al. |
| 6,299,621 | B1 | 10/2001 | Fogarty et al. |
| 6,368,340 | B2 | 4/2002 | Malecki et al. |
| 6,371,973 | B1 * | 4/2002 | Tepper .................. 606/205 |
| 6,425,867 | B1 | 7/2002 | Vaezy et al. |
| 6,602,251 | B2 | 8/2003 | Burbank et al. |
| 6,610,074 | B2 * | 8/2003 | Santilli .................. 606/158 |
| 6,635,017 | B1 * | 10/2003 | Moehring et al. .......... 600/439 |
| 6,905,506 | B2 * | 6/2005 | Burbank et al. ............ 606/205 |
| 2002/0111537 | A1 | 8/2002 | Taylor et al. |
| 2002/0165579 | A1 | 11/2002 | Burbank et al. |
| 2002/0183771 | A1 | 12/2002 | Burbank et al. |
| 2002/0188306 | A1 | 12/2002 | Burbank et al. |
| 2003/0018270 | A1 | 1/2003 | Makin et al. |
| 2003/0120306 | A1 | 6/2003 | Burbank et al. |

FOREIGN PATENT DOCUMENTS

| | | |
|---|---|---|
| DE | 200 22 012 U1 | 5/2001 |
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2 302 025 A | 1/1997 |
| GB | 2 311 468 A | 1/1997 |
| GB | 2302025 A * | 1/1997 |
| WO | WO 95/02370 | 1/1995 |
| WO | WO 95/02371 | 1/1995 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 99/11179 A | 3/1999 |
| WO | WO 01/68720 | 9/2001 |
| WO | WO 01/80713 | 11/2001 |
| WO | WO 02/00192 | 1/2002 |
| WO | WO 02/39904 A1 | 5/2002 |
| WO | WO 02/078521 | 10/2002 |

OTHER PUBLICATIONS

International Search Report for PCT/US2004/038111, mailed May 3, 2005.

Written Opinion for PCT/US2004/038111, mailed May 3, 2005.
Translation of FR 1 220 773.
International Search Report for PCT/US2004/038276, mailed Mar. 15, 2005.
International Search Report for PCT/US04/01935 mailed Feb. 15, 2005.
International Search Report for PCT/US04/03023 mailed Feb. 9, 2005.
International Search Report for PCT/US03/35815 mailed Jun. 30, 2004.
Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.
Bateman, William M.D., "Treatment of intractable menorrhagia by bilateral uterine vessel, Interruption", *Am. J. Obst. & Gynec.* 89(6):825-827 (Jul. 15, 1964).
Brigato, G. et al., "A Noninvasive Instrumental Method in Severe Postpartum Hemorrhages", *Minerva Ginecologica* 50(7-8):337-339 (1998).
Brohim, Robert M. et al., "Development of Independent Vessel Security After Ligation With Absorbable Sutures or Clips", *The American Journal of Surgery*, Mar. 1993, vol. 165, pp. 345-348.
Burbank, Fred et al., "Uterine Artery Occlusion by Embolization or Surgery for the Treatment of Fibroids: A Unifying Hypothesis-Transient Uterine Ischemia", *The Journal of the American Association of Gynecologic Laparoscopists*, Nov. 2000, vol. 7, No. 7 Supplemental, pp. S3-S49.
Fuchs, Karl, "Afibrinogenemia Treated by Ligation of Uterine Arteries", *Gynacologic* 148:407-411 (1959).
Garza Leal, J. et al., "Myoma Treatment by Transient Uterine Ischemia", *The Journal of the American Association of Gynecologic Laparoscopists* 7(3):S31 (Aug. 2000).
Hay, D.L. et al., "Hemostasis in Blood Vessels After Ligation", *Am. J. Obstet. Gynecol.*, Mar. 1989, 160:3, pp. 737-739.

Hunerbein, M. et al., "Endoscopic Ultrasound-Guided Real Time Biopsy of Peri-Intestinal Tumors", *Surgical Technology International VII*, 1998, pp. 91-95.
O'Leary, James A., M.D., "Uterine Artery Ligation in the Control of Postcesarean Hemorrhage", *The Journal of Reproductive Medicine, Inc.*, 40(3):189-193 (Mar. 1995).
O'Leary, James L., M.D. et al., "Uterine artery ligation in the control of intractable postpartum hemorrhage", *Am. J. Obst. & Gynec.* 94(7):920-924 (Apr. 1, 1966).
Ravina, J.H. et al., "Arterial Embolisation to Treat Uterine Myomata", *The Lancet*, Sep. 9, 1995, vol. 346, No. 8976, pp. 671-672.
Schaefer, C.J. et al., "Absorbable Ligating Clips", *Surg. Gynecol. Obstet.*, 1982, 154:513-516.
"Mick 200-TP Applicator Package", Mick Radio-Nuclear Instruments, Inc., advertisement.
"Multiplanar Biopsy Transverse Scan", Bruel U Kjaer Medical Systems, Inc., advertisement.
"Seeding Device—Proscan Urologic Ultrasound Imaging System", Teknar, advertisement.
Sonopsy Ultrasound Guided Breast Biopsy, NeoVision, advertisement.
"Transrectal Biopsy of the Prostrate Gland", Bruel & Kjaer Medical Systems, Inc., advertisement.
International Search Report for PCT/US02/09775 mailed Sep. 12, 2002.
International Search Report for PCT/US02/23347 mailed Nov. 20, 2002.
International Search Report for EP 99 96 7154 (PCT/US99/28101) mailed Dec. 3, 2002.
International Search Report for PCT/US02/22015 mailed Dec. 3, 2002.

* cited by examiner

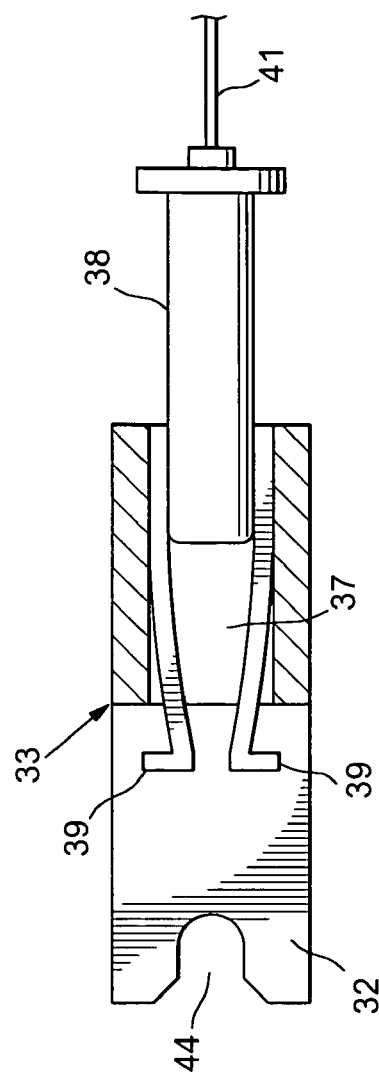
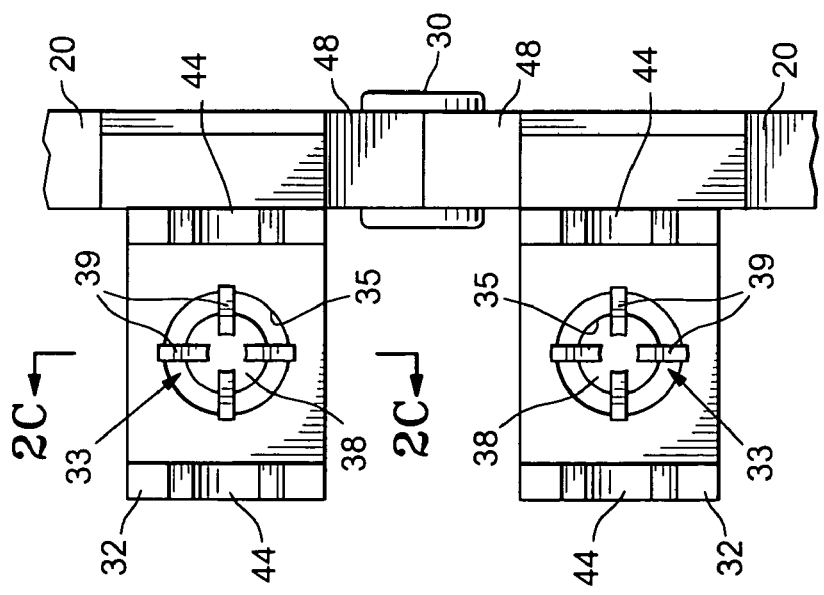
FIG. 2C
FIG. 2B

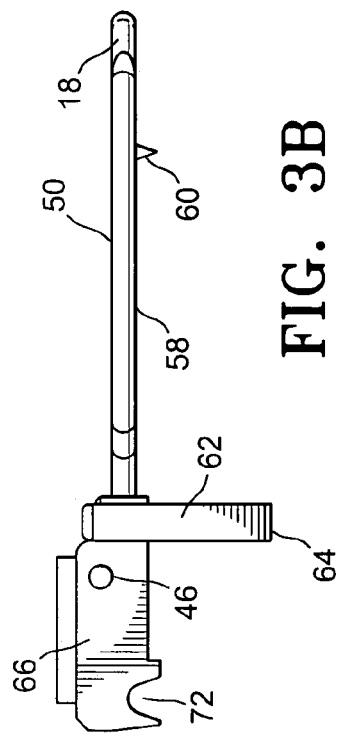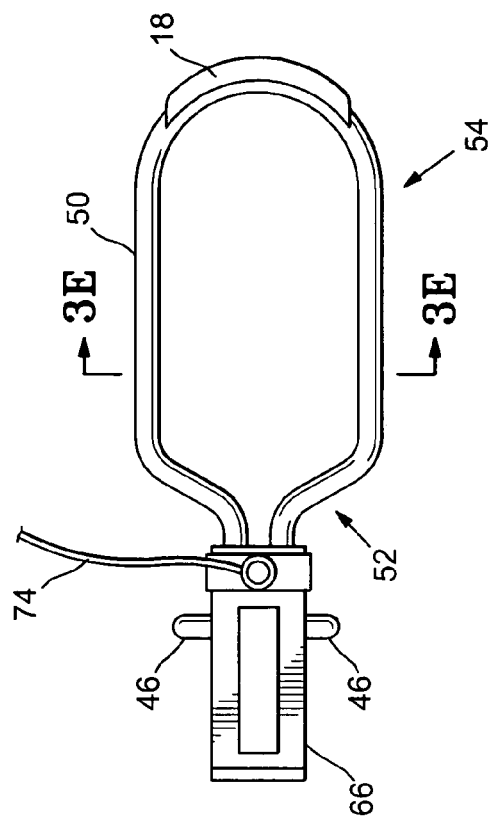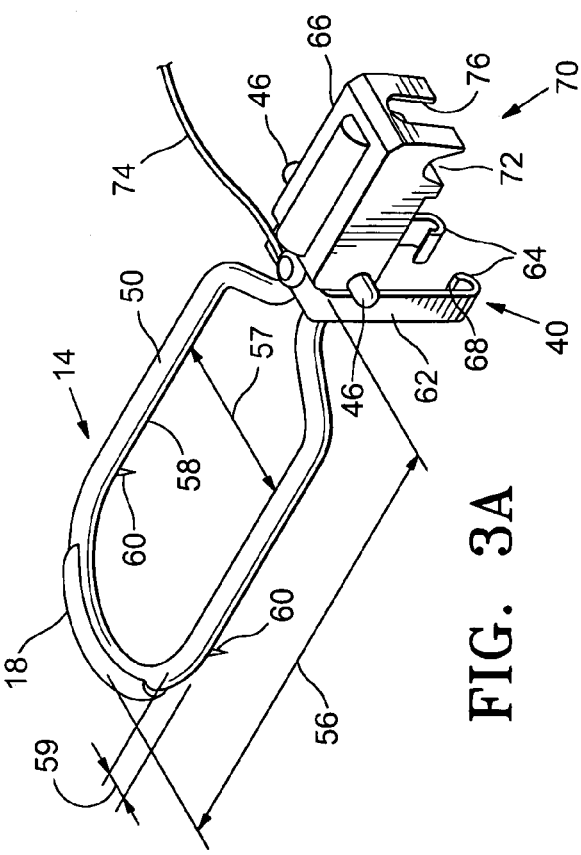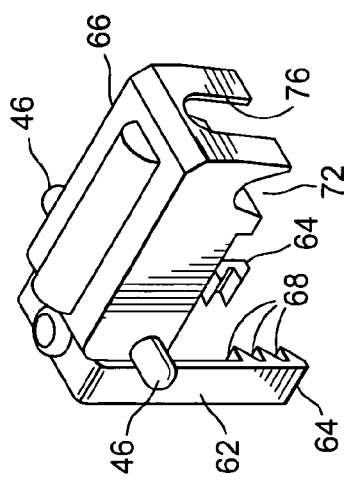
FIG. 3B
FIG. 3C
FIG. 3A
FIG. 3D

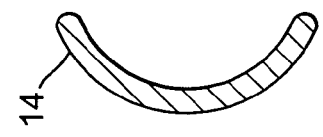
FIG. 3G
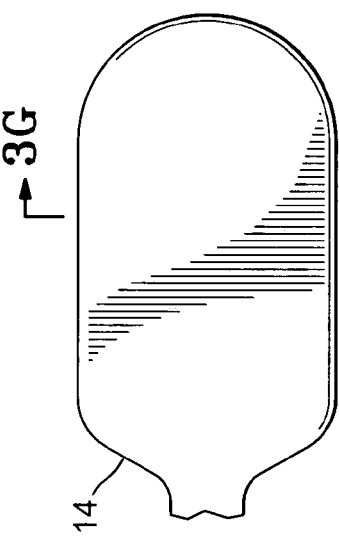
FIG. 3F
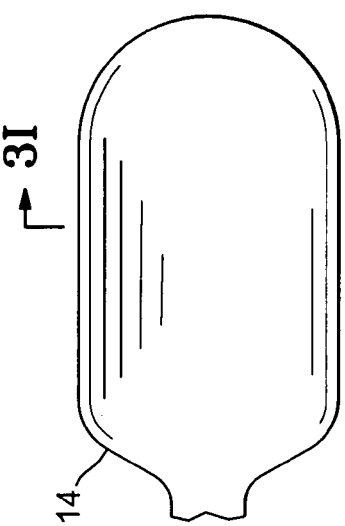
FIG. 3H
FIG. 3I
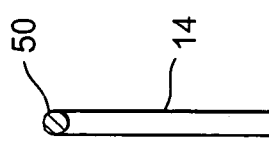
FIG. 3E

OCCLUSION DEVICE WITH DEPLOYABLE PADDLES FOR DETECTION AND OCCLUSION OF BLOOD VESSELS

CROSS-REFERENCE TO RELATED APPLICATIONS

This application is a continuation-in-part of U.S. patent application Ser. No. 10/107,810, filed Mar. 28, 2002, now U.S. Pat. No. 6,905,506 which claims priority from U.S. Provisional Patent Application 60/279,477 filed Mar. 28, 2001, both of which applications are hereby incorporated by reference in their entirety and from both of which priority is hereby claimed under 35 U.S.C. § 119(e) and 35 U.S.C. § 120.

FIELD OF THE INVENTION

The invention relates generally to the field of devices and treatments of diseases and conditions by the regulation of blood flow in blood vessels. In particular, the invention is directed to the treatment of uterine conditions by detecting and reducing or abolishing blood flow to the uterus.

BACKGROUND OF THE INVENTION

Hysterectomy (surgical removal of the uterus) is performed on approximately 600,000 women annually in the United States. Hysterectomy is often the therapeutic choice for the treatment of uterine cancer, adenomyosis, menorrhagia, prolapse, dysfunctional uterine bleeding (abnormal menstrual bleeding that has no discrete anatomic explanation such as a tumor or growth), and muscular tumors of the uterus, known as leimyoma or uterine fibroids.

However, hysterectomy is a drastic treatment, having many undesirable characteristics. Thus, any method which can approximate the therapeutic result of a hysterectomy without removing the uterus would be a significant improvement in this field. Newer treatment methods have been developed for some diseases which may spare these women a hysterectomy.

In 1995, it was demonstrated that uterine fibroids could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671-672, incorporated in its entirety herein). This technique is known as "uterine artery embolization". In this technique, uterine arteries are accessed via a transvascular route from a common femoral artery into the left and right uterine arteries.

The uterus has a dual (or redundant) blood supply, the primary blood supply being from the bilateral uterine arteries, and the secondary blood supply from the bilateral ovarian arteries. Consequently, when both uterine arteries are occluded, i.e. bilateral vessel occlusion, the uterus and the fibroids contained within the uterus are both deprived of their blood supply. However, as demonstrated by Ravina et al., the effect on the fibroid is greater than the effect on the uterus. In most instances, the fibroid withers and ceases to cause clinical symptoms. See also Burbank, et al., "Uterine Artery Occlusion by Embolization or Surgery for the Treatment of Fibroids: A Unifying Hypothesis—Transient Uterine Ischemia," The Journal of the American Association of Gynecologic Laparoscopists, November 2000, Vol. 7, No.4 Supplement, pp. S3-S49. U.S. Pat. No. 6,254,601, to Burbank et al., entitled "Methods for Occlusion of the Uterine Arteries," describes numerous devices and methods useful for occluding a uterine artery by penetrating the tissue of the patient to access the uterine artery.

However, catheter-based uterine artery embolization under radiologic direction is a complicated procedure, requiring special equipment and expertise. Accordingly, far fewer uterine artery embolizations than hysterectomies are performed for uterine fibroids which are symptomatic.

What is needed, therefore, are devices and methods to detect blood vessels and blood flow in blood vessels, and devices and methods to occlude blood flow in blood vessels such as the uterine arteries that can be used by physicians of ordinary skill in a simple medical setting or environment to aid in the therapeutic occlusion of arteries.

SUMMARY OF THE INVENTION

The invention provides devices, systems, and methods for detecting and occluding blood flow in a blood vessel. Such occlusion may be therapeutic or diagnostic; for example, uttering artery occlusion may be used to treat uterine disorders such as uterine fibroids, dysfunctional uterine bleeding, and other uterine disorders. A blood vessel occlusion device having features of the invention includes an applicator, a deployable pressure-applying member, and a location sensor. A location sensor may be configured to locate a blood vessel, and may include a blood flow sensor. An applicator having features of the invention may have a handle portion operatively connected with a force transduction element configured to aid in the transmission of force towards a pressure-applying member disposed at an applicator distal portion. A force transduction element may be, e.g., a pivot, and the handle portion may include a pair of shafts rotatably connected by a pivot, each of said shafts having a distal end and a proximal end. An applicator having features of the invention may further have an anchor element configured to releasably secure a pressure-applying member to the applicator.

A pressure-applying member having features of the invention has a tissue-contacting surface, and is configured to attach to the applicator, preferably to an anchor element of an applicator. A tissue-contacting surface of a pressure-applying member is configured to compress tissue. Pressure-applying members may be releasably secured to the applicator, having a first configuration in which they are attached to an applicator, and a second configuration in which they are released from the applicator. Pressure may be applied to tissue, and thus tissue may be compressed, in either of these configurations.

A pressure-applying member may be, e.g., a paddle configured to engage tissue; the engaged tissue is preferably near to a blood vessel. In preferred embodiments of devices having features of the invention, a pressure-applying member may be attached to a handle portion configured so that the paddle may be placed within a patient's body while a handle remains at least partly outside a patient's body and available for manipulation by an operator. Paddles are configured so as to compress tissue between pairs of paddles, effective to occlude a blood vessel near to or within the tissue. The paddles may be released from the handle after placement into contact with tissue and after compression of tissue is effected, allowing the removal of the handle while the paddles remain in place compressing tissue. Pressure-applying members may include tissue-retaining features such as spikes, rough surfaces, ridges, and scallops to aid in the attachment of the pressure-applying members to tissue.

A location sensor configured for locating a blood vessel is disposed in or on a pressure-applying member; in embodiments of the invention, the location sensor may be a blood flow sensor, such as a Doppler ultrasound sensor. A location sensor may be disposed on a tissue-contacting surface. A location sensor may be configured to operate with a sensor controller configured to provide a signal related to the sensor output that may be readily interpreted or used by an operator.

An applicator having features of the invention may also include an engagement element configured to engage a guide, such as a tenaculum. Engagement elements may include, for example, a ring, tube, or sleeve configured to engage and slide along at least a portion of the guide. In addition, embodiments of the invention include a locking mechanism having a locked configuration effective to retain the pressure-applying members in a pressure-applying configuration.

The invention also provides systems for occluding a blood vessel, comprising a blood vessel occlusion device with location sensor having features of the invention, and a guide configured to engage the engagement element. In preferred systems, the guide comprises a tenaculum, and the location sensor comprises a Doppler ultrasound sensor. Alternatively, a system may include a blood vessel occlusion device with a location sensor and sensor controller.

The invention also provides methods of occluding a blood vessel of a patient. The methods comprise locating a blood vessel with a location sensor of a blood vessel occlusion device having features of the invention, and compressing a portion of the blood vessel by applying pressure to tissue with the deployable pressure-applying members of the occlusion device, and may include releasing deployable paddles from a handle portion of an applicator, maintaining tissue compression for a suitable time, and maintaining tissue compression following release of deployable paddles. In further embodiments, the methods include guiding the blood vessel occlusion device with a suitable guide, such as a tenaculum or guidewire.

In preferred embodiments of the methods, the blood vessel occlusion device comprises a releasable blood vessel occlusion device configured to occlude a blood vessel for a limited time, and to release occlusion thereafter. A limited time may be sufficient to treat a condition in target tissue without causing undue damage or stress to other tissue. For example, in preferred methods, the limited time is sufficient to treat uterine fibroids without causing undue damage the uterus.

A method of occluding a uterine artery includes pushing a pressure-applying member of a device embodying features of the invention so as to distend a vaginal wall of a female patient near to a uterine artery, compressing the uterine artery with a pressure-applying member effective to reduce or abolish blood flow in the uterine artery. Compression may also be effective to retain the pressure-applying members in place.

Devices, systems and methods embodying features of the invention enable non-invasive identification and occlusion of blood vessels such as the uterine arteries. The devices and methods are simple and easy to use, enabling the occlusion of blood vessels without surgical intervention, and are simple to remove, thus providing many advantages over other methods and devices. Systems, devices and methods of the invention provide improved treatments for serious conditions and diseases, including uterine fibroids, adenomyosis, dysfunctional uterine bleeding (DUB), post-partum hemorrhage, and other uterine disorders. The devices, systems and methods embodying features of the invention thus provide tools and methods for effective treatment of diseases and conditions that might otherwise require invasive and irreversible treatments such as removal of a uterus.

BRIEF DESCRIPTION OF THE DRAWINGS

FIG. 2B is a face-on view of the applicator of FIG. 2A.

FIG. 2C is a longitudinal cross-sectional view of an anchoring element of the applicator shown in FIG. 2A.

FIG. 3A is a perspective view of a lower paddle portion of a device embodying features of the invention having a snap catch with a bracket having a single catch surface.

FIG. 3B is a side elevation view of a lower paddle portion of a device embodying features of the invention.

FIG. 3C is a top plan view of a lower paddle portion of a device embodying features of the invention.

FIG. 3D is a perspective view of a lower paddle portion of a device having a snap catch with a bracket having multiple catch surfaces embodying features of the invention.

FIG. 3E is a cross-sectional view taken along line 3E-3E of the paddle illustrated in FIG. 3C.

FIG. 3F is a top plan view of a planar solid paddle having features of the invention.

FIG. 3G is a cross-sectional view taken along line 3G-3G of the planar solid paddle illustrated in FIG. 3F.

FIG. 3H is a top plan view of a curved solid paddle having features of the invention.

FIG. 3I is a cross-sectional view taken along line 3I-3I of the curved solid paddle illustrated in FIG. 3H.

DETAILED DESCRIPTION OF THE PREFERRED EMBODIMENTS

Figure 1:
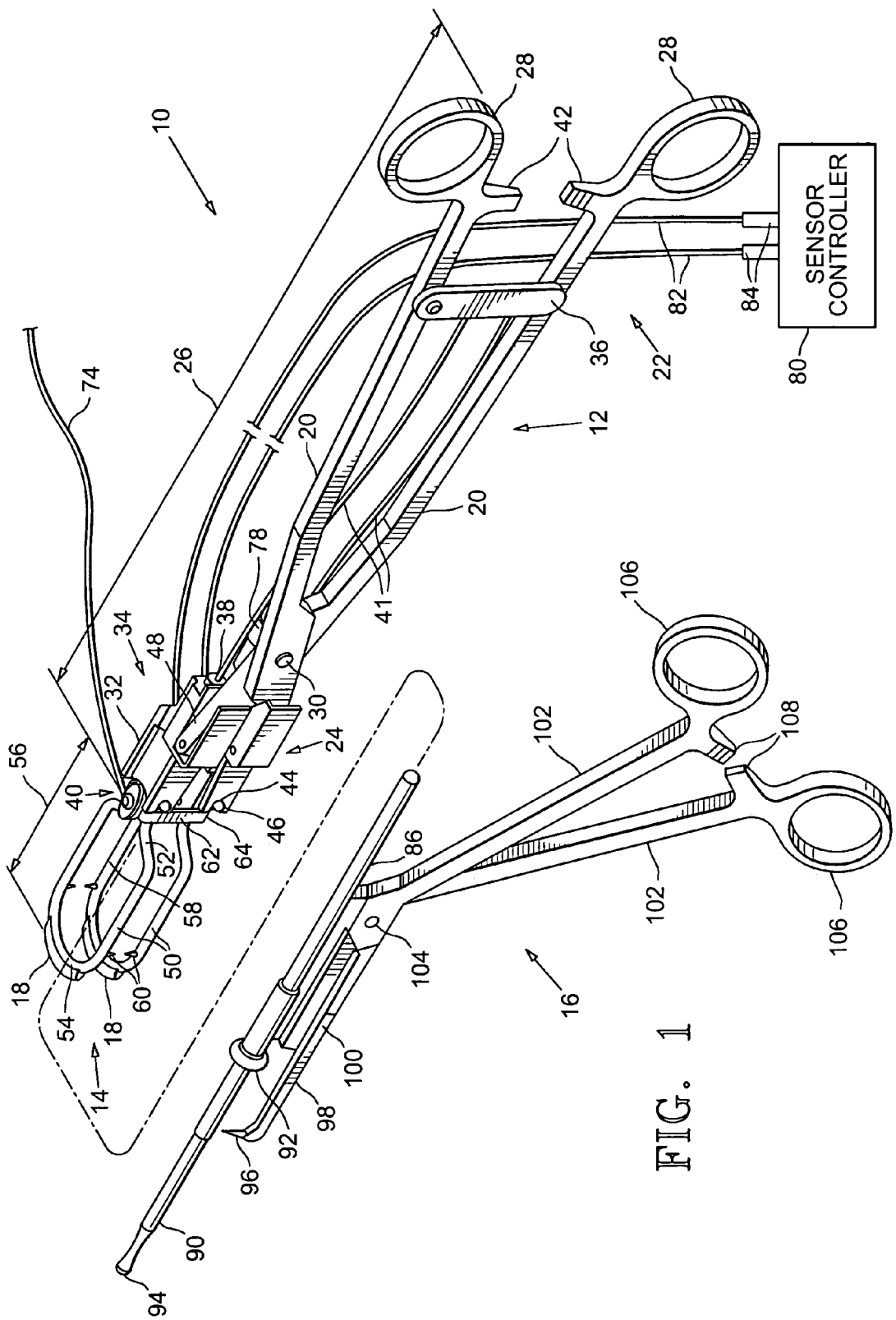
FIG. 1 is a perspective view of a system embodying features of the invention including an applicator with deployable paddles with location sensors and a tenaculum.

FIG. 1 illustrates components of a system 10 embodying features of the invention including an applicator 12, pressure-applying paddles 14 and a tenaculum 16. Paddles 14, having location sensors 18, are shown in FIG. 1 in an attached configuration, secured to the applicator 12, which is shown in a closed configuration. The tenaculum 16 and applicator 12 are separate and not engaged together in FIG.

Figure 2A:
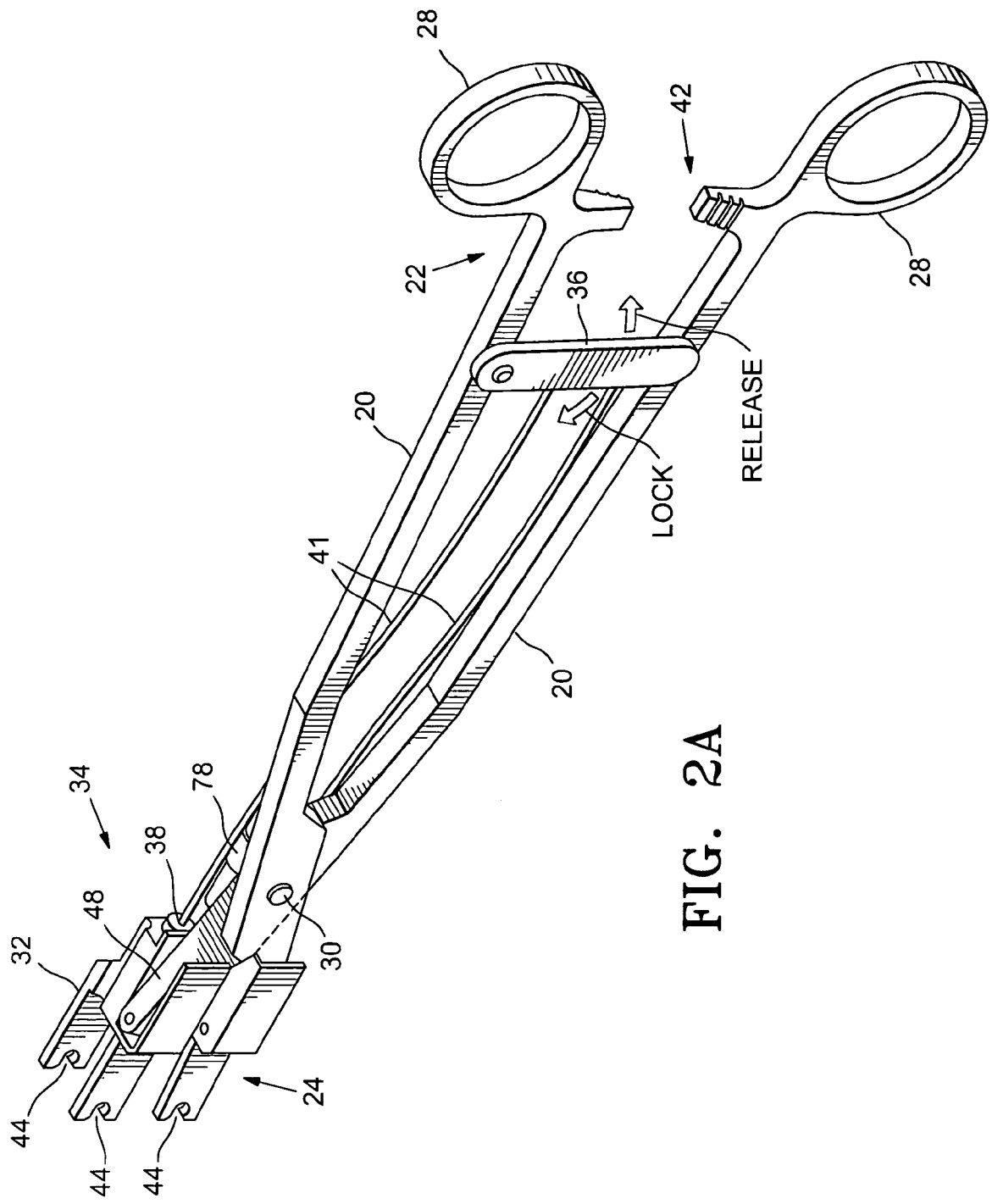
FIG. 2A is a perspective view of an applicator embodying features of the invention shown after paddle deployment.
Figure 4B:
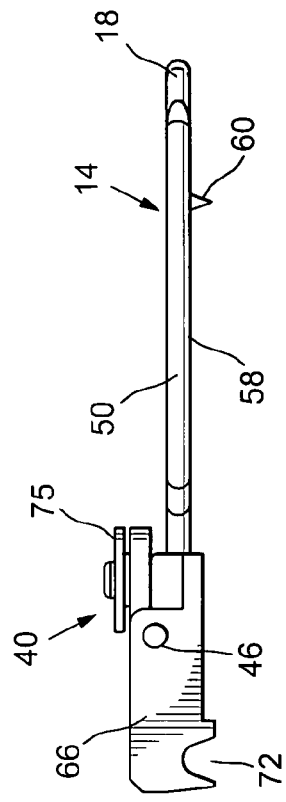
FIG. 4B is a side elevation view of an upper paddle portion of a device embodying features of the invention.
Figure 4C:
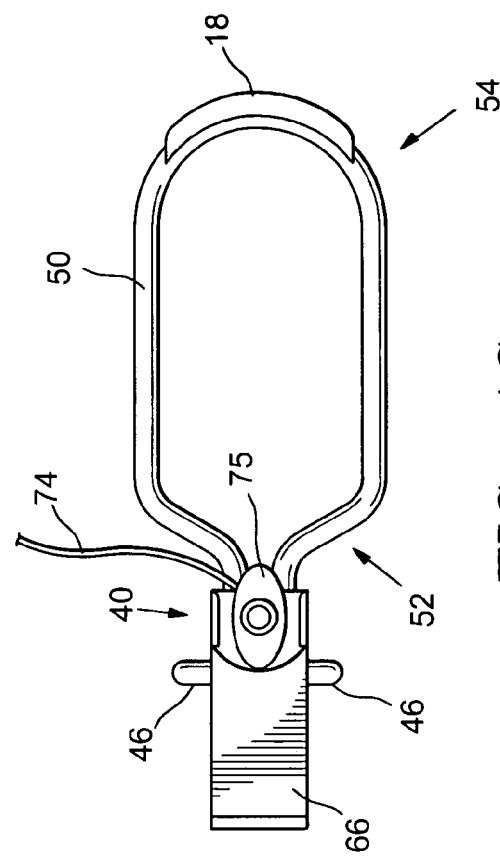
FIG. 4C is a top plan view of an upper paddle portion of a device embodying features of the invention.
Figure 4A:
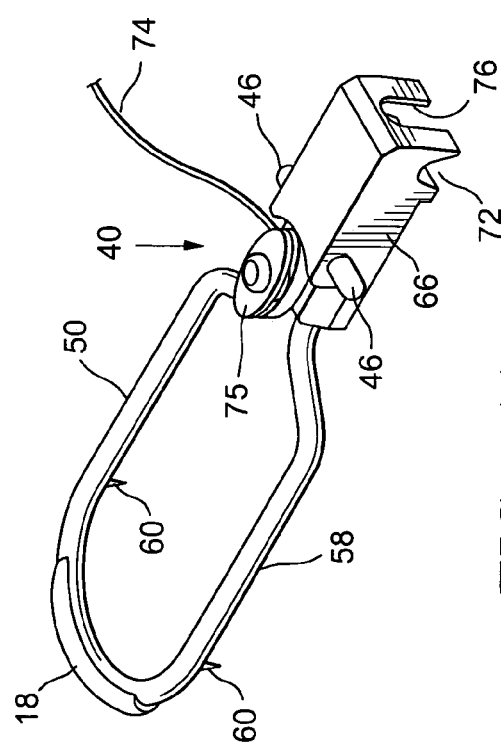
FIG. 4A is a perspective view of an upper paddle portion of a device embodying features of the invention.
Figure 5:
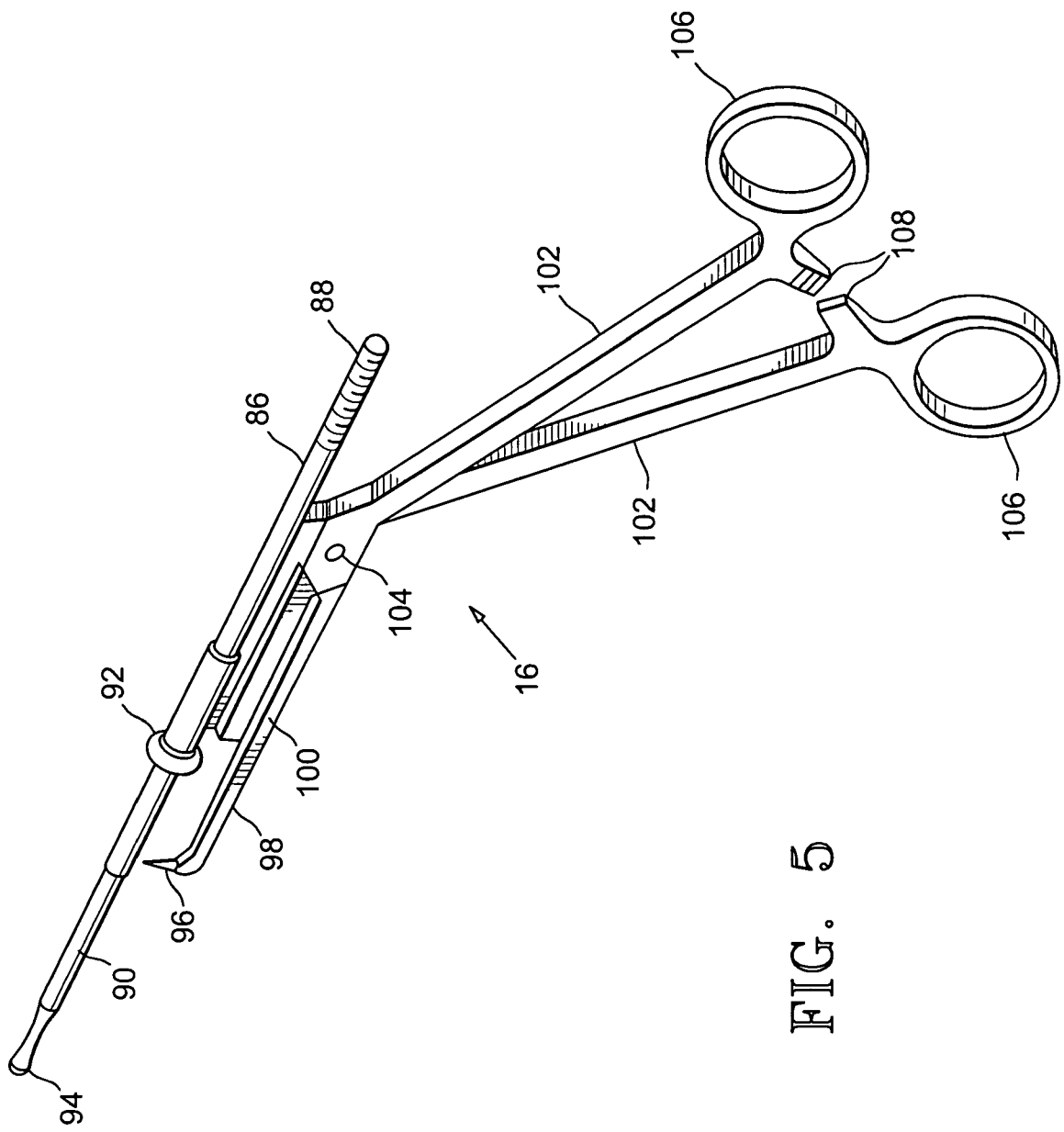
FIG. 5 is a perspective view of a tenaculum embodying features of the invention.
Figures 6A, 6B:
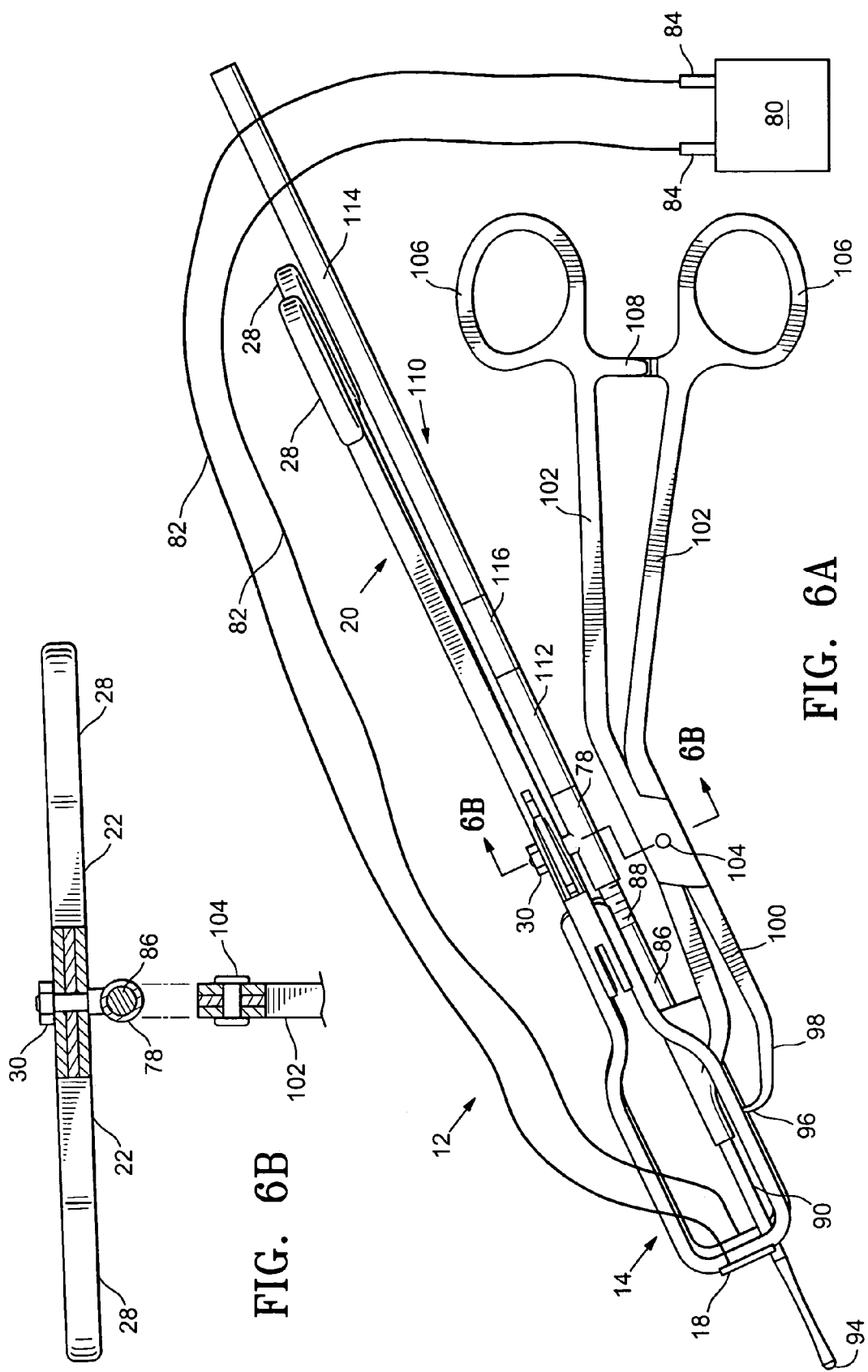
FIG. 6A is a perspective view of a system embodying features of the invention showing an applicator with deployable paddles engaged with a tenaculum.
FIG. 6B is a transverse cross-sectional view of the system of FIG. 6A taken at line 6B-6B.

1. These system components are also illustrated in various configurations in FIGS. 2-6. FIG. 2 shows an applicator 12 embodying features of the invention after deployment of paddles 14; an embodiment of paddles 14 having features of the invention is shown in greater detail in FIGS. 3A, 3B, 3C and 3D (lower paddle portion) and FIGS. 4A, 4B and 4C (upper paddle portion). A preferred embodiment of a tenaculum 16 having features of the invention is shown in FIGS. 5, 6A and 6B. FIGS. 6A and 6B illustrate a system 10 assembled with applicator 12 and attached paddles 14 mounted on a tenaculum 16. The system 10 in FIGS. 6A and 6B is configured to compress tissue, such as cervical tissue, effective to occlude a blood vessel located within the tissue (e.g., a uterine artery). A tenaculum 16 may serve as a guide to aid in the placement of an applicator 12, and may serve to stabilize an applicator 12 during application and deployment of paddles 14 by an applicator 12.

An applicator 12 having features of the invention has a handle or handles 20 with a proximal end (or ends) 22 and a distal end (or ends) 24 separated by a length 26. A length 26 is preferably configured to allow an operator to grasp a handle 20 while placing a paddle 14 within a patient's vagina adjacent a vaginal fornix or cervix of a female patient. A suitable length 26 may be, for example, a length of between about 3 inches and about 10 inches. As illustrated in FIGS. 1, 2, 6, and 8, an applicator 12 may include two handles 20 configured for co-operative use together to aid in the manipulation and control of the placement and action of paddles 14. Handles 20 are configured for manipulation by a human hand or hands; for example, in the embodiment shown in the figures, an operator may open or close the handles 20 by manipulation of the fingers engaged within finger holes 28. Handles 20 are configured to be able to move around pivot 30, transmitting the force applied by the operator in a desired direction. In other embodiments, a handle may comprise a single part also configured to aid in the manipulation and control of the placement and action of paddles 14, or, in further embodiments, may comprise more than two parts. A guide tube 78 configured to connect applicator 12 with a tenaculum 16 may be attached to pivot 30 as shown in the Figures, allowing rotation between a connected applicator 12 and tenaculum 16. In alternative embodiments, a guide tube 78 may be rigidly connected to an applicator 12, and may be connected at other locations besides a pivot 30. A guide tube 78 may be configured to slide along or over a tenaculum, allowing longitudinal translation of applicator 12 with respect to a tenaculum 16.

Anchoring elements 32 disposed at the distal ends of the handles 20 are configured to engage and retain paddles 14. As illustrated in FIG. 2, anchoring elements 32 comprise a supporting mechanism resembling a fork with two tines, having recesses 44 configured to receive and engage dowels 46 of the paddles 14. In addition, an expandable collet 33 forms part of release mechanism 34. An expandable collet 33 may be seated at least in part within a recess 35 within distal arms 48 disposed on a distal portion 24 of applicator 12. It will be understood that, in place of or in addition to a recess 35, an expandable collet 33 may alternatively be retained in place by struts, tabs, or other holding mechanisms. Release mechanism 34 is configured to help retain a paddle 14 in place on an applicator 12 when engaged with the paddle 14, and is configured to release the paddle 14 from applicator 12 when disengaged.

An example of an expandable collet 35 embodying features of the invention is shown in FIGS. 2B and 2C. A locking pin 38 is configured to fit at least partially within a bore 37 in the expandable collet 33, effective to press teeth 39 radially outwardly. Teeth 39 of expanding collet 33 engage a paddle 14 when in an expanded configuration, effective to hold paddles 14 securely on or adjacent distal arms 48 of handles 20. Teeth 39 of expanding collet 33 do not hold paddles 14 securely when not expanded, allowing for the release of paddles 14 when in a retracted configuration (e.g., when locking pin 38 has been retracted, allowing teeth 39 to collapse inwardly). Locking pins 38 may be retracted by pulling on release lever 36 connected to release lines 41, as illustrated in the Figures. Alternatively, a locking pin 38 may include a screw mechanism, and so be retracted by rotation effective to unscrew it; may include a cam mechanism, and so be retracted by rotation of the cam; or be retracted by another suitable mechanism.

As illustrated in the Figures, paddles 14 may also be connected to the rest of the applicator 12 with a three-point stability system to provide for lateral stability and to provide for varied geometry in contacting and in compressing tissue of various shapes and sizes. For example, dowels 46 may at least partially rotate around a longitudinal axis within recesses 44, allowing some freedom of movement to paddles 14 effective to adjust to and accommodate the particular sizes, shapes and compression resistance of various tissues as the tissues are compressed by paddles 14. Dowels 46 and recesses 44 may thus provide two of the three points of support in a three-point stability system connecting paddles 14 with applicator 12. The third point of support is provided by locking feature 70 (which serves as a pivot point, and has a recess 72 in paddle body 66) having a ridge 76 with which teeth 39 or other portion of an expandable collet 33 may engage. Ridge 76 is effective to retain paddle 14 and hold it in place on distal arm 48 of applicator 12.

An applicator 12 may be assembled together with a tenaculum 16. Embodiments of tenacula are described in the co-pending U.S. patent application "Tenaculum for Use with Occlusion Devices" by Fred H. Burbank et al., assigned to Vascular Control Systems, Inc., filed on the same day as the present application, the disclosure of which is hereby incorporated by reference in its entirety. When applicator 12 is assembled together with tenaculum 16, collar 92 of tenaculum 16 fits within and engages with locking feature 70, providing support from tenaculum 16 to paddles 14 and applicator 12. Thus, before deployment of the paddles 14, points of contact between paddles 14 and applicator 12 include contact between dowels 46 and the recesses 44 in distal arm portion 48 of handles 20, and contact between ridge 76 and expandable collet 33. Locking feature 70 and collar 92 may also be in contact with, and provide support to, components of the system 10.

A paddle 14 comprises a paddle frame 50 having a proximal portion 52 and a distal tip 54 separated by paddle length 56. A paddle inner surface comprises a tissue-contacting surface 58 configured to contact tissue and to adhere to or grip tissue with which it is in contact. A paddle 14 may have one or more tissue-gripping elements 60 disposed on or near tissue-contacting surface 58, such as spikes, teeth, bumps, ridges, edges, recesses, a rough surface, or other elements or features configured to improve adhesion between tissue and a paddle 14.

A paddle 14 may have an open paddle frame 50, or may be a solid paddle 14. A cross-section of a paddle 14 having an open paddle frame (taken along line 3E-3E of FIG. 3C) is shown in FIG. 3E. Examples of solid paddles 14 having features of the invention are illustrated in FIGS. 3F-3I. A planar solid paddle 14, with a substantially flat surface, is shown in FIGS. 3F and 3G; the cross-section in FIG. 3G is flat. A curved solid paddle 14, with a rounded surface, is shown in FIGS. 3H and 3I; the cross-section in FIG. 3I is curved. A curved solid paddle 14 may have a curved surface configured to approximate the curved surface of a cervix of a female patient.

A paddle 14 may be configured to join with an applicator 12 on a line substantially parallel to a line running along a handle 20, or may join at an angle to such a line. An angle between a paddle 14 and a handle 20 may be acute or may be obtuse. For example, the magnitude of an angle between a paddle 14 and a handle 20 may be about 20°, or about 30° angle, or about 135°, or any other angle.

Paddles 14 are configured to apply pressure to tissue by capturing and compressing tissue between them when closed together, effective to at least partially occlude blood vessels within tissue. Tissue compression is thus effective to reduce or abolish blood flow within a blood vessel disposed within the tissue captured between a pair of paddles 14. For example, manipulation of handles 20 so that finger holes 28 are brought more closely together is effective to bring paddles 14 more closely together. Paddles 14 and tissue contacting surfaces 58 are configured to contact tissue without causing excessive tissue damage during tissue compression.

Tissue compression is also effective to hold paddles 14 in place attached to tissue captured between a pair of paddles 14. Such compression may be effective to occlude a blood vessel not located between a pair of paddles 14. For example, when paddles 14 are pressed inwardly against a vaginal fornix so as to compress a uterine artery by forcing it against a uterus or other internal structure, retention of paddles 14 in place attached to tissue is effective to maintain the pressure required to reduce or abolish blood flow within a blood vessel not disposed between a pair of paddles 14.

Sufficient pressure and compression is effective to completely occlude a blood vessel located within compressed tissue, and thereby to abolish blood flow within the blood vessel. Temporary compression does not typically lead to irreversible damage or occlusion to the blood vessel; thus, upon release of the compression, blood flow returns to normal.

An effective amount of pressure, suitable for occluding a blood vessel by compressing a blood vessel or tissue adjacent a blood vessel, is typically between about 3 pounds per square inch (psi) and about 200 psi, preferably between about 5 and about 80 psi, more preferably between about 7 psi and about 10 psi.

Tissue compression may be maintained as long as the paddles remain in place, spaced closely together in a compressing configuration. It will be understood that the compressing configurations in which paddles 14 are held more closely together provide more pressure and more tissue compression than configurations in which paddles 14 are held less closely together. Handles 20 may be locked into a closed configuration by ratchet 42, which may be located on a proximal end of a handle, as may be desired when applying pressure to tissue with paddles 14. Ratchet 42 is configured to retain handles 20 in a desired, pressure-applying position, holding paddles 14 closely together in one of several compressing configurations while paddles 14 remain attached to handles 20. Ratchet 42 is a releasable locking mechanism, so that tissue compression may be relieved while paddles 14 remain attached to handles 20 by release of ratchet 42 and withdrawal of applicator 12 and paddles 14.

Paddles 14 may detach from an applicator 12. Detachment of paddles 14 may be effected while paddles 14 are held closely together in contact with tissue in a compressing configuration, as well as in other configurations. Release mechanism 34 is configured to allow the detachment and deployment of paddles 14 from applicator 12 after placement on, and compression of, body tissue, effective to occlude a blood vessel within the body tissue. In the embodiment illustrated in FIGS. 1-6, paddle release may be activated by movement of release tab 36 connected to release lines 41 to withdraw locking pin 38 at least partially from within bore 37 of expandable collet 33, moving locking pin 38 into a releasing configuration and thus releasing engagement between collet 33 and locking feature 70 so as to allow paddle 14 to detach from handle 20. It will be understood that alternative release mechanisms may be used in addition to, or in place of, the example illustrated in the Figures. For example, clips, pins, clamps, threads, and other releasable securing devices may be used to retain and release deployable paddles 14 from applicators 12 of devices and systems 10 having features of the invention.

Paddles 14 are configured to remain together in a compressing configuration after release from applicator 12. A yoke mechanism 40 is configured to link paddles 14 together, and to hold paddles 14 together so as to maintain pressure on tissue disposed between paddles 14. In a preferred embodiment illustrated in the Figures, yoke mechanism 40 includes snap catch 62 having bracket 64 configured to engage a paddle base 66. A bracket 64 may have one or more surfaces configured to grip and retain a paddle base 66. In an open configuration, paddles 14 are separated and yoke mechanism 40 is not engaged with paddle base 66. Closure of handles 20 moves paddles 14 more closely together. Sufficient closure brings bracket 64 into contact with a paddle base 66. Snap catch 62 is configured to flex, allowing bracket 64 to move so as to allow paddle base 66 of lower paddle 14 to continue to move towards opposite paddle base 66 of upper paddle 14 as handles 20 and paddles 14 approach one another. Snap catch 62 acts like a spring, forcing bracket 64 against the lateral surface of paddle base 66. Further closure brings bracket 64 around and past the basal surface of paddle base 66 so that a catch surface 68 is able to secure paddle base 66, by, for example, snapping into place around paddle base 66. Force from snap catch 62 presses bracket 64 to move inwardly so as to capture paddle base 66, thereby securing paddles 14 together in a closed, compressing configuration. A bracket 64 may have more than one catch surface 68 configured to catch and retain a paddle base 66. Where a bracket 64 has multiple catch surfaces 68, closure together of the paddles 14 engages first the outermost catch surface 68, then, with further closure, more inwardly situated catch surfaces 68. Where yoke mechanism 40 has a bracket 64 with only a single catch surface 68, paddles 14 have only one secured, compressing configuration. Where a yoke mechanism 40 has a bracket 64 provided with multiple catch surfaces 68, paddles 14 have multiple secured, compressing configurations.

Yoke mechanism 40 is configured to hold paddles 14 together, once paddles 14 have been brought closely together, whether the paddles 14 are attached to applicator 12 or not. In the embodiment illustrated in FIGS. 3 and 4, paddle body 66 has a locking feature 70 configured to engage an applicator 12, and has a recess 72 configured to receive a fulcrum on which the paddle 14 may pivot when engaged with a tenaculum 16. Release mechanism 34 of an applicator 12, including release tab 36 and locking pin 38 engaged with an expandable collet 33, is configured to hold locking feature 70 until release is desired. In the embodiment illustrated in FIGS. 1-3, locking feature 70 includes a ridge 76 with which expandable collet 33 may engage. Movement of release tab 36 connected to release lines 41 is effective to pull locking pin 38, effective that locking pin 38 no longer presses within bore 37 of expanding collet 33, so that teeth 39 of expanding collet 33 no longer engage ridge 76 in paddle base 66, releasing paddle 14 from applicator 12. It will be understood that alternative designs and configuration for releasably attaching paddles 14 to distal arms 48 of an applicator 12 are also suitable for devices and systems embodying features of the invention.

The paddles 14 are deployable (may be released from the applicator 12) within the vagina 122, allowing removal of the applicator 12 while paddles 14 remain in place, thus minimizing discomfort and allowing for patient movement during treatment. Such treatment may include, for example, placement of paddles 14 around a patient's cervix to apply pressure to occlude a uterine artery 130 or 132 or uterine arteries 130 and 132. The paddles 14 may be deployed from the applicator 12 while locked together at various angles and with various distances separating the paddles 14 and paddle bases 66 (these variations may be collectively termed "variable geometry"). In this way, devices and methods embodying features of the invention are able to accommodate physical differences between patients. Such accommodation may be accomplished, for example, by providing multiple locking points and positions effective to hold the paddles together at one of a variety of angles and separations. The multiple-position snap catch illustrated in FIG. 3D allows for such varied geometry.

In preferred embodiments of the devices, the paddles 14 use a three-point stability system to provide for both the varied geometry and lateral stability. During initial application of the paddles 14, points of contact include the recesses 44 on the applicator 12 and the locking feature 70 on the paddle bodies 66. The locking feature 70 with recess 72 may receive portions of expanding collet 33 (e.g., teeth 39), thus helping to join paddles 14 with an applicator 12. When released from the applicator 12 and the locking feature 70 on the paddle bodies 66, points of contact include the snap catch 62 and ridge 76.

A paddle 14 may have at least one attached lanyard 74 to aid in the recovery of the paddle 14 after the paddle 14 is released from the applicator 12. A lanyard 74 may further be configured to release snap catch 62, allowing separation of a pair of paddles 14, releasing tissue compression and aiding detachment of paddle 14 from a patient's tissue, while also aiding in the recovery of the paddles 14. For example, a lanyard 74 may be configured to rotate release cam 75 so as to expand snap catch 62 and bracket 64 to allow paddles 14 to release compression on enclosed tissue, to separate and to be removed.

In further embodiments, paddles 14 may be secured or locked together by a variety of mechanisms. Features which may be included in an applicator 12 embodying features of the invention in order to hold the paddles 14 during deployment and which allow for the variable geometry at release of the paddles 14 include at least the following six features labeled A through F. (A) Enlarging the recess 72 in the locking feature 70 that holds the paddles 14 to the applicator 12 allows for greater amounts of pivoting to occur, and allows for a greater volume in which to detect and locate a blood vessel. (Such enlarging may include providing a locking feature 70 with recess 72 that may expand during use). (B) Enlarging the anchoring elements 32 gives stability during use and allows for greater pivoting of the paddles 14. (C) Providing leaf springs which control the position of the paddles 14 connected to the anchoring elements 32 helps to prevent the release of the paddle bodies 66 from the expanding locking feature 70 that might occur during excessive rotation. (D) A release mechanism may be included to allow for the actuation of the expanding locking feature 70. (E) A ratchet at the back of the applicator 12 acts as a locking mechanism 42 to provide stability to the system 10 until blood vessel occlusion is verified and release of the paddles 14 is desired. (F) An applicator 12 may be configured to work over, around, or adjacent the tenaculum 16 by, for example, aligning handles 20 in a plane perpendicular to a plane containing the handles 102 of the tenaculum. A tenaculum 16 may also be configured to work over, around, or adjacent the applicator 12 by, for example, angling the tenaculum handles 102 downward and away from the attachment region for the applicator (e.g., away from guide rail 86 where guide tube 78 engages).

At least one paddle 14 of a pair of paddles 14 has a location sensor 18. As illustrated in the Figures, a location sensor 18 may be located at a distal tip 54 of a paddle frame 50. It will be understood that a location sensor 18, or multiple location sensors 18, may be positioned at other locations as well. A location sensor 18 (or location sensors 18) is disposed on a frame 50 of a paddle 14 positioned effective to detect blood flow in a blood vessel when the paddle 14 is near to or in contact with tissue having a blood vessel.

A location sensor 18 may be any sensor, including a sensor for locating a blood vessel and including a sensor configured for detecting blood flow. A location sensor 18 may be passive (detecting intrinsic signals indicating the presence of a blood vessel) or active (producing a signal and detecting a response to it). A location sensor 18 may thus be a sound location sensor (e.g., a microphone capable of sensing blood flow sounds), an ultrasound sensor, a pressure transducer, stress gauge or strain gauge to detect pulsations in a blood vessel due to heart action, an electromagnetic location sensor (e.g., infrared location sensor) to detect a blood vessel (e.g., to detect hemoglobin), a pH or other chemical location sensor, or other location sensor.

Ultrasound reflected by moving blood cells undergoes a frequency shift. Ultrasound reflected back from blood cells moving away from the ultrasound source has a lower frequency than the source ultrasound frequency; ultrasound reflected back from blood cells moving towards the source has a higher frequency than the source frequency. This Doppler frequency shift phenomenon can be measured by transceiver electronics and sent to a speaker to create sounds detectable by an operator. For example, a change in blood velocity may be signaled by a change in the frequency (i.e., pitch) of the loudspeaker output signal, or by the volume of the loudspeaker output signal.

Preferably, a location sensor 18 is a Doppler ultrasound sensor, configured to emit and to detect ultrasound signals effective to detect blood flow and to locate a blood vessel. Doppler ultrasound systems typically include a sensor controller that may include an electrical connector to plug in the location sensor, a power switch to power-on the transceiver electronics, an audible speaker output so that an operator can hear the Doppler frequency shift, a volume adjustment to control overall sound level, and batteries or other power source to provide energy. A location sensor 18 may be operably connected to a sensor controller 80 by a sensor cable 82. A sensor controller 80 is preferably configured to receive information from location sensor 18, and may also provide power to location sensor 18, may serve as a signal source, a signal output (e.g., may provide an audible sound related to the location sensor output) and may control the operation of the location sensor 18. In use, a sensor controller 80 is typically situated outside a patient's body and connected to a location sensor 18 disposed on or within a patient's body. A sensor controller 80 may connect with a single location sensor 18, or with multiple location sensors 18. Commercially available Doppler ultrasound sensors and sensor systems suitable for use in the present invention include the Koven model ES 100× MiniDop VRP-8 probe (St. Louis, Mo.), the DWL/Neuro Scan Medical Systems' Multi-Dop B+ system (Sterling, Va.), and the MedaSonics® CardioBeat® Blood Flow Doppler with Integrated Speaker (Cooper Surgical, Inc., Trumbull Conn. 06611)).

To detect blood flow in the uterine arteries, ultrasound transducers may be placed within a vagina. Ultrasound transducers may, for example, point axially into the patient's tissue and insonate it up to a depth of approximately 3 cm (attenuated through tissue) for 8 MHz systems. The bilateral uterine arteries run laterally inward from sidewall of pelvis to the uterus just behind the vaginal mucosa near the cervix, and are by far the single largest blood vessels in this area, making their detection by ultrasound relatively straightforward. In addition, the inventors have discovered that a Doppler crystal may be optimized for uterine vessel detection by configuring it to detect blood flow in a wide region detected by the location sensors.

The frequency of the ultrasound energy used for Doppler ultrasound will change the viewing angle of the ultrasound system. One aspect of the present invention is the use of Doppler crystals (serving as both a location sensor 18 and as an ultrasound source) which permit Doppler data to be gathered at distances up to about 3 cm from a paddle 14. When a paddle 14 on which a Doppler crystal is mounted is pushed against the vaginal wall at the vaginal fornix, the Doppler crystals will receive reflected signals from the uterine artery of interest. Thus, while many different Doppler crystals are suitable in the present invention, those which operate at frequencies between about 5 MHz and 20 MHz, preferably between about 6 MHz and about 10 MHz, more preferably at a frequency of about 8 MHz have been found to be particularly suitable.

A location sensor 18 may also be, for example, an infrared or other electromagnetic location sensor. Electromagnetic energy useful for sensing a location of a blood vessel or of blood flow in a blood vessel may have a wavelength of between about 500 nanometers (nm) and about 2000 nm, preferably between about 700 nm and about 1000 nm.

A location sensor 18 is preferably mounted on a distal tip 54 of a paddle 14. For example, a blood flow sensor may be mounted at a paddle distal tip 54, or may be mounted near to a distal tip 54, e.g., no farther than between about 0.1 inch and about 1 inch from the distal tip 54 of a paddle 14. A location sensor 18 preferably has a sensing direction, in which a blood vessel that is located along a sensing direction is detectable by the location sensor 18. A sensing direction may be defined with respect to a tissue-contacting surface 58 of a paddle 14 in which a location sensor 18 is disposed. A sensing direction typically includes a range of directions within a solid angle taken effective that a blood vessel disposed at least in part in or across the solid angle of a sensing direction is detectable by a location sensor 18. Thus, a location sensor 18 may be configured to indicate the location of a blood vessel with respect to a paddle 14. A location sensor 18 is typically disposed on or within a pressure-applying member so that its sensing direction is substantially parallel to a tissue-contacting surface 58 of a paddle 14. Such a sensing direction is effective to locate blood vessels or detect blood flow in arteries to disposed in a direction generally parallel to a tissue-contacting surface 58, i.e., generally parallel to a paddle length 56 and within a solid angle of between about 20° and about −20° with respect to the tissue-contacting surface 58. However, other sensing directions are also suitable, including, for example, sensing directions that are substantially perpendicular to a tissue-contacting surface 58 (i.e., within a solid angle of between about 70° and about 110° with respect to the tissue-contacting surface 58).

In preferred embodiments, a paddle 14 will include at least one, and optionally a plurality of location sensors 18 comprising Doppler ultrasound crystals oriented with the viewing direction of the crystals pointed in a distal direction. Doppler ultrasound crystals may preferably be positioned at the distal face of a paddle 14 so that data derived from the signals received by the Doppler crystals can be more easily correlated to the distance of the uterine artery from the distal end. A location sensor 18 may be integrated into a paddle frame 50 of a paddle 14, e.g., molded into the paddle 14 itself, or alternatively can be removably mounted in or on a paddle 14.

A sensor cable 82 may have a connector 84 configured to be received in a receptacle on or in a sensor controller 80, or may be permanently or semi-permanently connected to a sensor controller 80. A connector 84 is preferably a reversible connector configured to readily engage and disengage with a sensor controller 80. Alternatively, a cable 82 may directly and permanently engage a sensor controller 80 without having a connector 84 (e.g., may be soldered, brazed, welded, secured by a screw, or otherwise securely connected). A cable 82 connecting location sensor 18 with a sensor controller 80 may include an electrical cable, an optical fiber, a waveguide, other conduit for carrying energy or signals, or a combination of these.

In embodiments of the invention, it may be advantageous to provide only one, or only a few, location sensors 18 (e.g., one or a few Doppler ultrasound crystals) for sensing blood flow. A limited number of location sensors 18 provides information that may be simply interpreted and evaluated. For example, the output of a single Doppler ultrasound crystal may be directed to a sound system to provide an audible signal to be monitored by the operator of the system 10. A change in the frequency of the audible signal or in another audible characteristic of the signal, is useful to identify the presence of a blood vessel in tissue near the location sensor, and is typically readily understood by an operator. Alternatively, a plurality of Doppler ultrasound crystals may be advantageous in providing more data about the flow of blood through an artery of interest than would be available from a single location sensor 18. It will be understood that the additional data derived from multiple location sensors 18 may require additional manipulation that can increase the complexity and cost of the device.

When used, a tenaculum 16 may function as a guide and as a fixed mounting point for the applicator. The sound 90 of the tenaculum 16 may be inserted without trauma into the cervical os 124, providing a structure for guiding subsequent placement of an applicator 12 and paddles 14. The tenaculum 16 may function with an applicator device to provide stability to the cervix during application of the paddles 14 to the cervix 124. The tenaculum 16 is useful to guide the paddle 14 attached to the applicator 12 into place on the cervix 124, and may be used as a mount or lock for the deployable paddles 14 during initial placement and for the duration of the occlusion. Alternatively, in embodiments of the invention in which the paddles 14 have a spike 60 or spikes 60, or other elements configured to retain the paddles 14 in place on the cervix 124, the tenaculum 16 may be removed after placement of the paddles 14 and application of pressure to the cervix 124 and or vaginal fornix 128 effective to occlude a uterine artery 130 or 132.

A tenaculum 16 may be used to aid in the placement of paddles 14 and to provide a stable foundation for compression of tissue effective to occlude a blood vessel. As exemplified by the tenacula 16 illustrated in FIGS. 1, 5 and 6, a tenaculum 16 includes a guide rail 86 (which may have threads 88) and a sound 90, which are preferably collinear and may comprise parts or ends of a single beam or column, and a fulcrum 92. A guide rail 86 may be between about 1 inch and about 10 inches long, and is preferably between about 3 inches and about 6 inches in length. A guide rail 86 is preferably configured to be received by guide tube 78 of applicator 12 so that an applicator 12 may be securely mounted on a tenaculum 16. For example, in preferred embodiments of devices having features of the invention, a guide rail 86 may be between about 0.125 inches and about 0.25 inches in diameter. Whether a guide rail 86 is smooth (as illustrated in FIG. 1) or has threads 88 (as illustrated in FIGS. 5 and 6) a guide tube 78 may be configured to slide longitudinally along the guide rail 86. Handles 102 of a tenaculum 16 may lie generally along a line making an angle with a guide rail 86, or may form an angle bisected by such a line, where the angle may be between about 10° and about 30°, preferably between about 15° and about 20°.

Fulcrum 92 may be configured to be received by a recess 72 in a paddle base 66. A pair of recesses 72 may at least partially enclose a fulcrum 92, aiding in the secure attachment between paddles 14 and a tenaculum 16. Such an attachment between paddles 14 and a tenaculum 16 may remain a secure attachment even after the release of paddles 16 from an applicator 12. Sound 90 of tenaculum 16 has a distal tip 94 configured for entry into a cervical os of a female patient. Distal tip 94 is preferably rounded in order to reduce the possibility of trauma to the cervix and uterine canal and to reduce possible discomfort to the patient. In embodiments of devices and systems having features of the invention, a distal portion of a tenaculum 16 may detach from a proximal portion (e.g., from a handle or handles 102) while remaining engaged with paddles 14 and with a patient's tissue.

Closure of tenaculum handles 102 (e.g., by pressing tenaculum finger holes 106 closer together), rotating fixation arm 100 around pivot 104, is effective to press spike 96 into tissue to retain tenaculum 16 in place. A spike 96 disposed on a distal portion 98 of fixation arm 100 is effective to retain tenaculum 16 in place after being pressed into tissue (e.g., into a cervix of a female patient). In embodiments of devices having features of the invention, a fixation arm 100 may have a length of between about 1.5 and about 4 inches, preferably between about 2.5 to about 3 inches. It will be understood that a tenaculum 16 may include multiple spikes 96, and that other retention elements configured to retain a tenaculum in place within or on a patient's body may be used with or in place of a spike 96.

A spike 96, or other retaining element, allows an operator to pull on or otherwise manipulate a patient's tissue with a tenaculum 16. Such manipulation of a patient's tissue may be desirable to place the tissue in a desired position or orientation; for example, pulling on a cervix extends the cervix so as to provide a better configuration for placement of paddles 14 and for occlusion of uterine arteries. A ratchet 108 configured to lock handles 102 into a closed configuration is effective to maintain fixation arm 100 in position so as to maintain pressure on tissue for as long as desired.

Placement of a distal tip 94 of a sound 90 within a patient's cervix serves to locate the tenaculum 16 in a position effective to guide the placement of paddles 14 onto and around a cervix so as to aid in the location and occlusion of uterine arteries of a female patient. A sound 90, and particularly a distal tip 94, is preferably configured to contact tissue without causing undue trauma. In embodiments of devices having features of the invention, a tenaculum sound 90 may be between about 1 inch and about 5 inches, preferably between about 1.5 inches and about 2.5 inches in length. A tenaculum sound is preferably malleable or flexible. A sound 90 and distal tip 94 may be made, at least in part, with materials such as silver, silver alloys, or other biocompatible materials. A sound 94 made at least in part with a silver or silver alloy may be pliable, so that a clinician may readily adjust the tip to conform to the anatomy and clinical presentation of an individual patient if desired.

As shown in FIG. 6A, a locking tube 110 may be attached to, or mounted on, a guide rail 86. A locking tube 110 may be configured to engage a guide rail 86 by having a distal end 112 (which preferably has a bore with internal threads) configured to engage threads 88 of a guide rail 86. A locking tube 110 may also have a proximal handle portion 114, connected to the distal portion 112 by a connecting portion 116. In preferred embodiments, a connecting portion 116 is flexible; for example, a connecting portion 116 may be a piece of flexible tubing sized to tightly engage the distal 112 and proximal 114 portions. Rotation of a locking tube 110 is effective to advance the distal end 112 of locking tube 110.

FIGS. 6A and 6B illustrate an assembled system 10 with applicator 12 mounted on tenaculum 16 with paddles 14 attached to distal arms 48 of handles 20. Such a system is configured to apply pressure to tissue effective to occlude a blood vessel. As shown in FIG. 6A, distal end 112 of locking tube 110 contacts a guide tube 78 of an applicator 12 when a locking tube 110 is screwed onto a guide rail 86 after the guide tube 78 of an applicator 12 has been mounted on guide rail 86 of tenaculum 16. FIG. 6B illustrates the assembled system in a cross-section, taken along line 6B-6B shown in FIG. 6A through guide tube 78 and guide rail 86 distal of the contact between locking tube 110 and guide tube 78. Rotation of locking tube 110 so as to advance the locking tube 110 in a distal direction along threads 88 of guide rail 86 is effective to push on guide tube 78 of applicator 12, moving applicator 12 longitudinally with respect to tenaculum 16, and advancing paddles 14 into tissue when the system 10 is in place in contact with the tissue of a patient. An example of the use of a system 10 having features of the invention, in which blood flow through uterine arteries is reduced or abolished by compression of cervical tissue, is described below.

Figure 7:
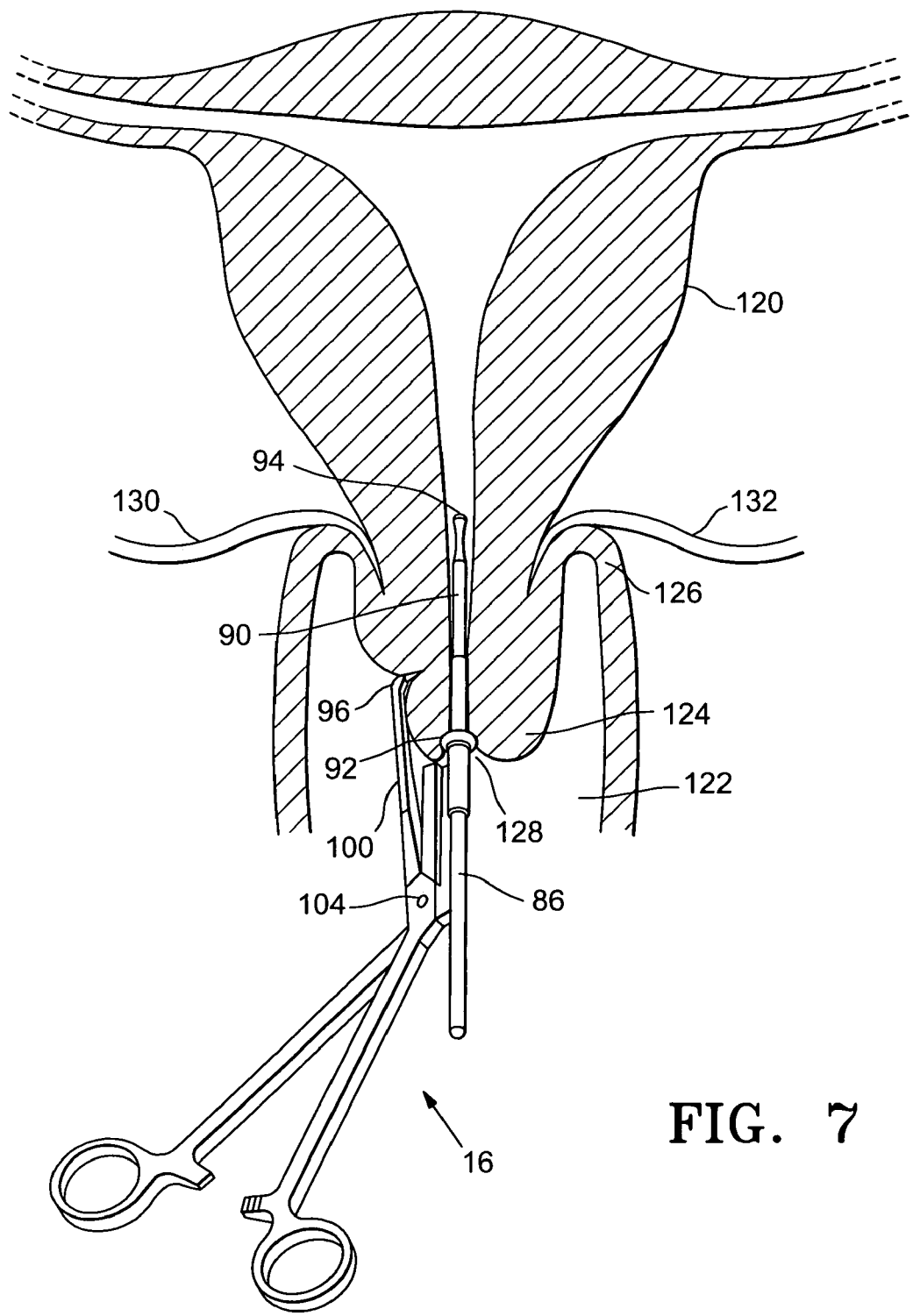
FIG. 7 is a schematic cross-sectional diagram showing a tenaculum in place within a patient's body.
Figure 8:
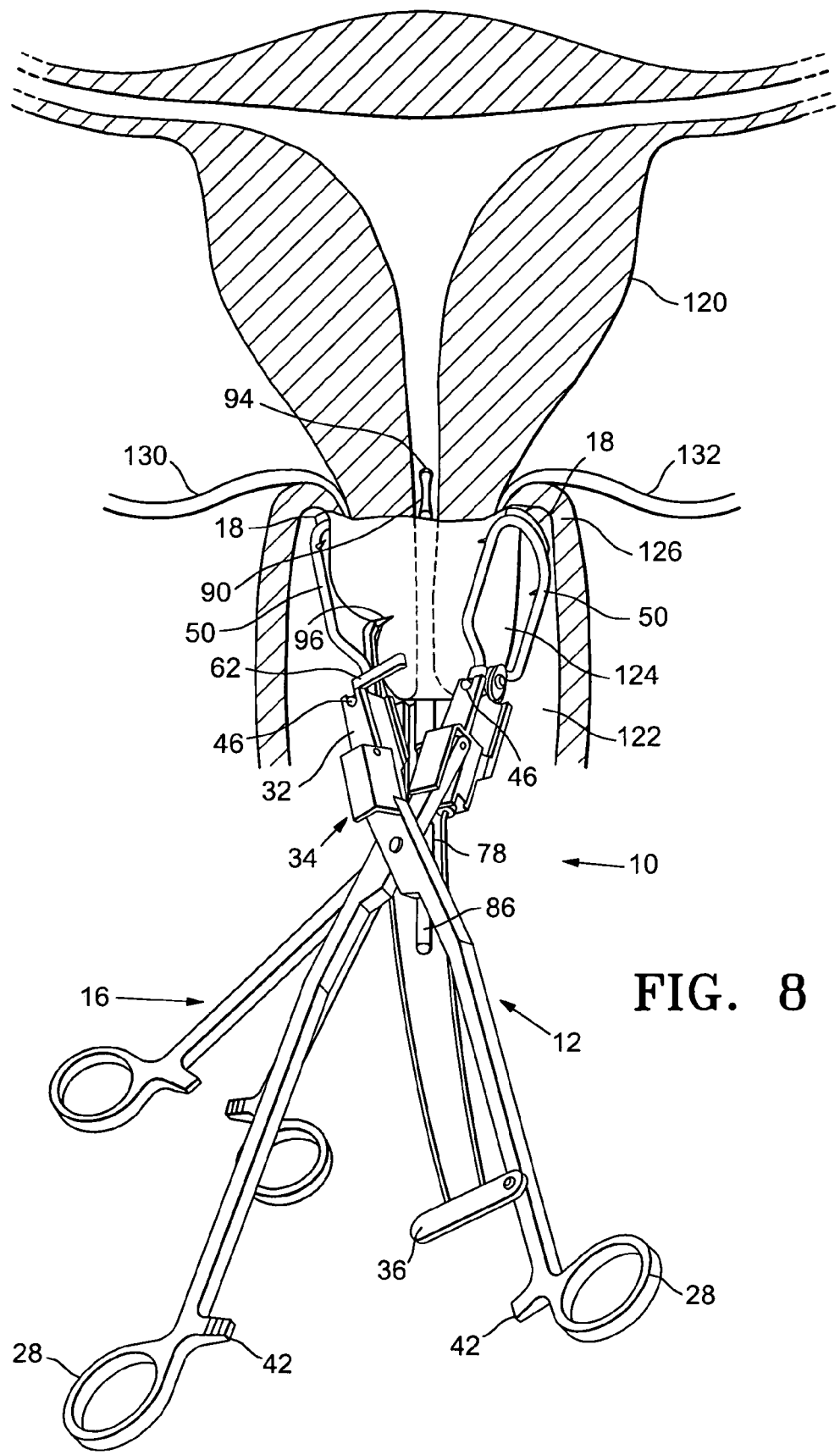
FIG. 8 is a schematic cross-sectional diagram showing an applicator with deployable paddles mounted on a tenaculum in place within a patient's body.
Figure 9:
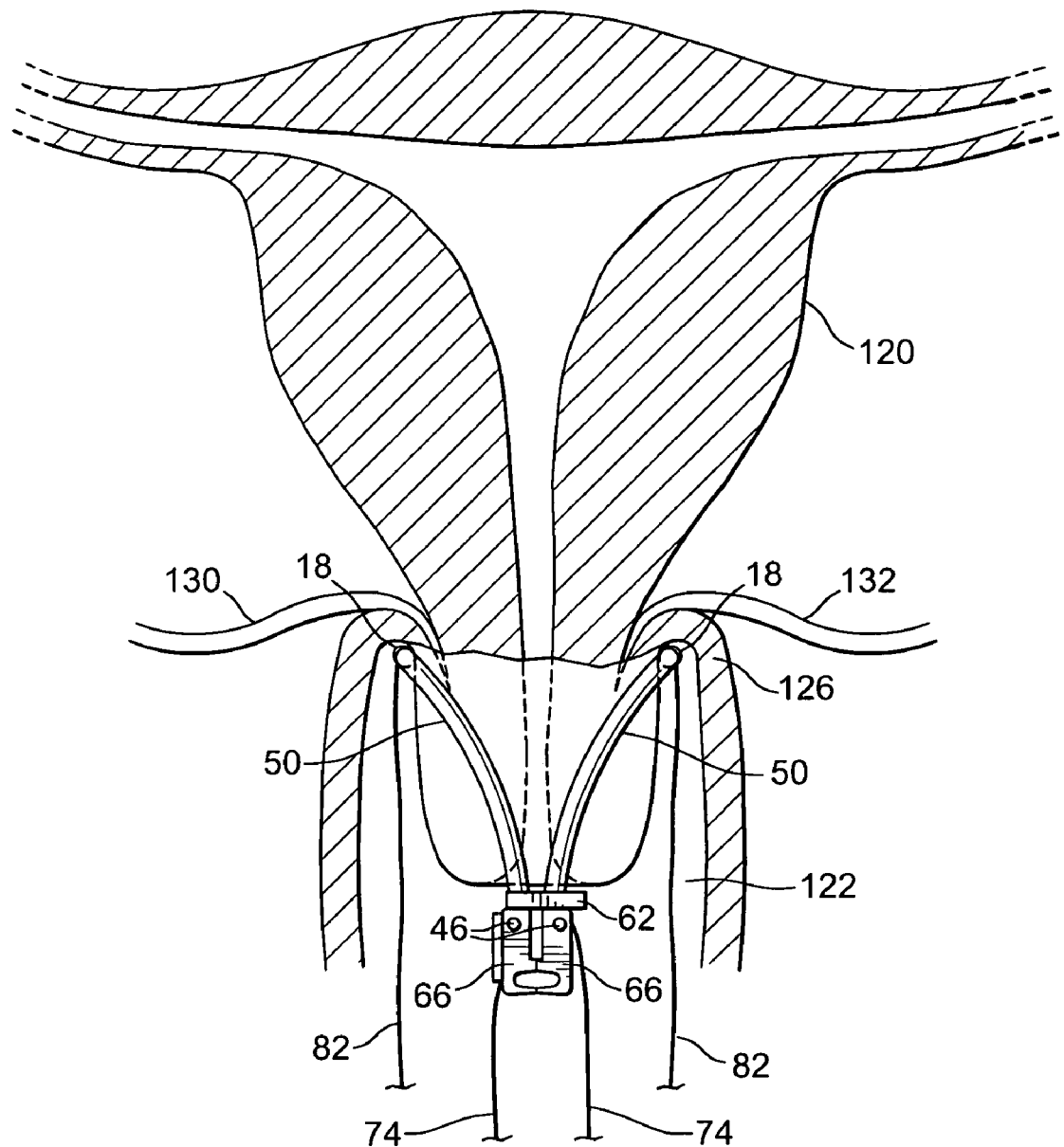
FIG. 9 is a schematic cross-sectional diagram showing deployable paddles in place within a patient after their release from the applicator and after removal of the applicator and tenaculum.

FIGS. 7, 8 and 9 include schematic diagrams of female human reproductive anatomy and related structures. Uterus 120 may be accessed via vagina 122 and cervix 124. A vagina 122 has a wall extending to form the vaginal fornix 126 adjacent cervix 124. Cervix 124 may be approached by medical instruments such as a system 10 having features of the invention. Cervical os 128, located at the apex of the cervix 124, provides an opening into the uterus 120. The blood supply to the uterus 120 derives from the aorta and the iliac arteries, with right uterine artery 130 and left uterine artery 132 branching off the iliac arteries, while ovarian arteries branch from the aorta. The uterus 120 thus has at least two sources of blood supply: the uterine arteries 130 and 132, and the ovarian arteries. It is believed that, in most women, the uterine arteries provide the more significant fraction of the uterine blood supply.

The uterine arteries of female humans are typically disposed about 3 cm or less from the vaginal wall near the vaginal fornix 126 where a uterine artery 130 or 132 meets the uterus 120, although the uterine arteries for a single patient sometimes are spaced at slightly different distances. When one assigns a 12 o'clock position to an anterior portion of the uterus (e.g., approximately facing a patient's navel), the left uterine artery 132 is typically disposed at a position between about the 1 and 5 o'clock positions, and more frequently between about 2 and 4 o'clock. There is typically symmetry between the uterine arteries, i.e., that the right uterine artery 130 is typically disposed at a position between about the 7 and 11 o'clock positions, and more frequently between about 8 and 10 o'clock. The cervix 124 can be used as a platform and a landmark from which to locate and access a uterine artery 130 or 132 because of the axial symmetry of the cervix 124 and its generally cylindrical or frustoconical exterior shape. The uterus 120, because it is a muscular and generally firm mass, can be used as a backstop or anvil against which a uterine artery 130 or 132 can be compressed. See also U.S. application Ser. No. 09/908,815, filed Jul. 20, 2001, to Fred Burbank et al. ("'815 application"), co-assigned with the present application, the entire contents of which are incorporated by reference herein, for additional discussions of the anatomy of the uterus, cervix, and vaginal wall.

Methods and devices embodying features of the invention may be used to occlude any blood vessel. A method of occluding a blood vessel includes sensing a blood vessel (which may include detecting and/or locating a blood vessel), and compressing a blood vessel with a clamping device having a location sensor, so that blood flow through the blood vessel is reduced or is abolished. The location sensor may be a blood flow sensor, and is preferably a Doppler ultrasound blood flow sensor. Sensing a blood vessel may include sensing blood flow, such as sensing blood flow in a blood vessel. In the following discussion, the uterine artery is used as an example of a blood vessel to be occluded. It will be understood that the methods and devices discussed in regard to this example may also be applied to any other artery, vein, or other blood vessel.

Thus, in an embodiment of a method of the invention, a method of occluding a blood vessel of a patient comprises locating a blood vessel with a location sensor disposed on a pressure-applying member of a blood vessel occlusion device; and compressing at least a portion of the blood vessel with one or more pressure-applying members of the blood vessel occlusion device. The location sensor is preferably a Doppler ultrasound blood flow sensor. The pressure-applying members are preferably the paddles 14 of a system 10. The methods may further comprise guiding the blood vessel occlusion device with a guide, which is preferably a tenaculum. In preferred embodiments of the methods, the blood vessel is a uterine artery.

Compressing a blood vessel may include grasping tissue near to a blood vessel, and may include compressing tissue surrounding a blood vessel effective to compress the artery. The methods of the invention may further include detecting a reduction in blood flow in a blood vessel. The methods may further comprise locking a device into a compressing configuration.

Location sensors 18 may be used to establish that the blood flow through the uterine artery or arteries has been reduced or stopped. Such a reduction or cessation may be observed for a therapeutically effective period of time, after which time a practitioner can release the compression from the uterine artery, and remove the paddles from the patient. The term therapeutically effective time and its equivalents are used as in U.S. patent application Ser. No. 09/556,934, filed Apr. 21, 2000, by Burbank et al., and U.S. patent application Ser. No. 09/908,815, filed Jul. 20, 2001, by Burbank et al., both of which references are hereby incorporated by reference herein.

In preferred methods, a uterine artery remains occluded for only a limited time. A suitable limited time may be between about 0.5 hour and about 24 hours, preferably between about 0.5 hour and 12 hours, or more preferably between about 1 hour and about 8 hours. Compression may be released by release of a ratchet 42 where the paddles remain attached to an applicator 12; or, compression may be released by use of a lanyard 74 to release yoke mechanism 40 retaining compression between paddles 14 released from an applicator 12.

FIG. 7 is a schematic diagram illustrating the placement of a tenaculum 16 embodying features of the invention partially into the cervical os 128 within the vagina 122 of a female human patient. The tip 94 of sound 90 is gently inserted into the cervical os 128 of a patient, orienting and guiding the tenaculum 16 so that guide rail 86 will be properly aligned for subsequent guidance of an applicator 12 for the placement of paddles 14 around cervix 124 of a patient's uterus 120. It is preferred to place the tenaculum 16 in position before mounting the applicator 12 onto the tenaculum 16. Closure of tenaculum handles 102 brings arm 98 towards cervix 124 within vagina 122 and presses spike 96 into cervix 124, providing secure engagement of the tenaculum 16 in place. The secure engagement between tenaculum 16 and cervix 124 may be used to pull, or otherwise maneuver, the cervix 124 as needed by the operator. For example, pulling on cervix 124 may be useful to place uterine arteries 130 and 132 into closer apposition to the vaginal fornix 128 or uterus 120, or both, and so to aid in subsequent compression of these arteries by paddles 14. As illustrated in FIG. 8, tenaculum 16 is shown pulling on cervix 124 so that uterine arteries 130 and 132 are pressed between uterus 120 and vaginal fornix 128.

FIG. 8 is a schematic diagram illustrating the use of a system 10 embodying features of the invention in the occlusion a uterine artery 130 or 132, and preferably both, of a female human patient, showing an applicator with deployable paddles 14 mounted on a tenaculum 16 in place within a vagina 122 and partially inserted in to a cervical os 128 of a female patient. Location sensors 18 on paddles 14, placed within vagina 122 and against tissue such as vaginal fornix 128 may be used to sense blood flow in the uterine arteries 130 and 132, aiding in their detection and location.

A location sensor 18 is effective to detect and locate a uterine artery 130 or 132, aiding in positioning paddles 14 and tissue-contacting surfaces 58 to best approach the uterine artery 130 or 132 or tissue near these arteries. Closing paddles 14 presses tissue-contacting surfaces 58 together, compressing uterine artery 130 or 132, effective to occlude uterine artery 130 or 132. Location sensor 18 may further be used to detect the resulting reduction or abolition of blood flow in uterine artery 130 or 132, and to adjust the amount of force used in order to effect the desired amount of reduction in blood flow and to confirm abolition of blood flow if desired. A locking mechanism 42 may be used to maintain the desired amount of force on the tissue for a desired amount of time. Blood flow in the right uterine artery 130 may be similarly occluded.

Pushing a paddle 14 toward a uterine artery causes the uterine artery (and adjacent tissues) to be pinched between the distal end of the paddle 14 and the uterus 120, using the uterus 120 is used as an 'anvil' against which the uterine artery is compressed effective to trap or pin the uterine artery against the uterus 120. Thus, pushing on a paddle 14 compresses the uterine artery, at least partially, and optionally completely, stopping the blood flow through the artery. Cessation of blood flow through the uterine artery can have beneficial effects for the patient, including the treatment of fibroids by limiting the blood supplied to the fibroids in the uterus.

In FIG. 8, paddles 14 are shown pressing vaginal fornix 128 onto uterus 120 and cervix 124, compressing uterine arteries 130 and 132, effective to reduce or abolish blood flow within these arteries. Such a reduction or abolition of blood flow may also be sensed by location sensors 18, and is useful to verify the correct application of the paddles, to monitor the progress of the procedure, and to verify its success. Both uterine arteries 130 and 132 may be occluded at the same time by application of paddles 14 as shown.

Deployable paddles 14 may be released from applicator 12 by action of release mechanism 34. FIG. 9 is a schematic diagram illustrating the use of a system 10 embodying features of the invention in the occlusion a uterine artery 130 or 132 of a female human patient following deployment of paddles 14 from an applicator 12. Deployable paddles 14 are shown in place within a patient effecting the occlusion of the uterine arteries 130 and 132, after their deployment from the applicator 12 and after the removal of the applicator 12 and tenaculum 16 from within the patient's vagina. Tissue compression may be maintained after deployment, by action of yoke mechanism 40 and related elements. Thus, after application of compression, and securing of paddles 14 together in a compressing configuration by yoke mechanism 40, paddles 14 may be released from applicator 12 and applicator 12 removed from the vagina of the patient while compression and blood vessel occlusion is maintained, so that blood flow remains reduced or abolished. Tenaculum 16 may remain in place, or, alternatively, tenaculum 16 may also be removed while paddles 14 remain engaged in a compressing configuration in place within a patient.

Paddles 14 have a release mechanism which releases the snap catch and allows for the separate paddle bodies 66 to be removed. For example, a lanyard 74 may be engaged with a release cam 75, so that pulling on lanyard 74 rotates release cam 75 expanding snap catch 62. Alternatively, a lanyard 74 may remove a snap catch pin which can be removed, or other mechanism effective to allow for the separation of paddle bodies 66. Resumption of blood flow may be detected and monitored following release of compression. Where paddles 14 remain attached to applicator 12, release of pressure on handles 20, by, for example, release of ratchet 42 is effective to release tissue compression.

The paddle frame 50 is sized and configured so that it can compress a uterine artery. A pair of paddles 14 may be used together to compress one or both uterine arteries 130 and 132 of a patient. Thus, according to particularly preferred embodiments, the paddle frame 50 is formed with a length 56 of between about 0.5 inches and about 5 inches, more preferably between about 1 and about 2 inches, and with an inner paddle width 57 of between about 0.5 inch and about 2.5 inches, preferably between about 0.7 inches and about 1.3 inches, and more preferably about 0.8 inches. Additionally, the outer diameter or dimension of the material out of which the frame 50 is formed is selected to balance strength, the ability to form the material into the desired shape of the loop, and to transmit sufficient force to a uterine artery to compress it. Preferably, the frame 50 has a cross-sectional diameter 59 of between about 0.07 inches and about 0.2 inches, more preferably between about 0.12 inches and about 0.16 inches, yet more preferably about 0.14 inches.

Blood vessel-occluding devices embodying features of the invention may be made from any suitable material or combination of materials, including metals such as stainless steel and shape memory alloys such as nickel titanium alloys, other biocompatible and preferably sterilizable metals, plastics, ceramics, and other materials known in the art. Biocompatible polymers, such as biocompatible and sterilizable thermoplastic and thermoset materials such as for example, polycarbonate, polysulfone, polyester, polyethylene, polyacetal, and other polymers may be particularly suitable for embodiments of the invention. It will be understood that devices and systems may comprise any one or combinations of these and similar materials. The device or system may be designed for single use (disposable) or may be sterilizable and capable of being used multiple times.

The present invention also relates to devices, systems, and processes which can be useful in treating dysfunctional uterine bleeding (DUB). Other aspects of the present invention relate to treating a patient who is diagnosed with DUB by compressing one or both uterine arteries, either serially or simultaneously, so that the uterine blood supply is greatly diminished or completely cut off. Without the blood supplied by the uterine arteries, the uterus stops bleeding, which can permit the medical practitioner to better diagnose the patient's condition. The reduction in blood flow resulting from uterine artery occlusion may be itself used as a treatment for DUB; that is, the DUB will not reoccur upon reestablishment of the blood supply to the uterus through the uterine arteries, the uterus being 'reset' by going through a period of induced anoxia or hypoxia or clotting cycle.

The present invention also includes as an aspect the treatment of bleeding associated with Caesarian section. Devices and/or methods of the present invention can be used to slow or stop blood flow to the uterus through the uterine arteries immediately after a baby is delivered by Ceasarian section. Subsequently, Caesarian incision repair can be performed in a manner that optimizes surgical closure without worry about blood loss control at the time of closure.

The present invention also includes as an aspect the treatment of bleeding associated with Post Partum Hemorrhage (PPH). PPH is defined in the medical literature as the estimated loss of more than 500 ml of blood following delivery of a baby. According to aspects of the present invention, when it is recognized that bleeding has not stopped normally as it should after delivery, devices and/or methods in accordance with the present invention can be employed as described herein to slow or stop PPH. Preferably, paddles 14 may have paddle lengths 56 that are longer when configured for PPH than for other clinical treatments. For example, a paddle length 56 configured for treatment of PPH may be between about 0.8 inches and about 6 inches, preferably between about 2.5 inches and about 4.5 inches, more preferably about 3.5 inches.

While particular forms of the invention have been illustrated and described, it will be apparent that various modifications can be made without departing from the spirit and scope of the invention. Accordingly, it is not intended that the invention be limited to the specific embodiments illustrated. It is therefore intended that this invention to be defined by the scope of the appended claims as broadly as the prior art will permit, and in view of the specification if need be. Moreover, those skilled in the art will recognize that features shown in one embodiment may be utilized in other embodiments. Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action. All patents and patent applications referred to above are hereby incorporated by reference in their entirety.

What is claimed is:

1. A uterine artery occluding device, comprising:
   a. a first elongated handle member which has a proximal handle portion, a distal handle portion and a first releasable paddle base receiving member on the distal handle portion;
   b. a first paddle member having a pressure applying surface at a distal end configured to engage a portion of a female patients vaginal fornix and occlude an underlying uterine artery and a paddle base on a proximal end configured to fit in the paddle base receiving member of the first elongated pressure applying member so as to fix the orientation of the first paddle member with respect to the first handle member;
   c. a second elongated handle member which has a proximal handle portion, a distal handle portion and a second releasable paddle base receiving member on the distal handle portion;
   d. a second paddle member having a pressure applying surface at a distal end configured to engage a portion of a female patients vaginal fornix and occlude an underlying uterine artery and a paddle base on a proximal end configured to fit in the base receiving member of the second elongated pressure applying member so as to fix the orientation of the second paddle member with respect to the second handle member;
   e. at least one of the paddle members having a releasable locking element configured to lock together the paddle bases and a lock releasing element that is configured to release locked paddle bases independent of the first and second handle members;
   f. a pivotal connection between the first and second pressure applying members at a location proximal to the releasable paddle base locking members and distal to the proximal handle portions thereof; and
   g. a blood flow sensor disposed on the pressure applying surface of at least one of the releasable paddles.

2. The uterine artery occlusion device of claim 1 wherein said blood flow sensor is selected from the group of sensors consisting of sound sensors, ultrasound sensors, pressure sensors, pulsation sensors, stress sensors, strain sensors, chemical sensors, electromagnetic radiation sensors, and combinations thereof.

3. The uterine artery occlusion device of claim 2, wherein said sensor comprises an ultrasound sensor.

4. The uterine artery occlusion device of claim 3, wherein said ultrasound sensor comprises a Doppler ultrasound sensor.

5. The uterine artery occlusion device of claim 4, wherein said Doppler ultrasound sensor is configured to sense ultrasound energy having a frequency of between about 5 MHz and about 20 MHz.

6. The uterine artery occlusion device of claim 4, wherein said Doppler ultrasound sensor is configured to sense ultrasound energy having a frequency of between about 6 MHz and about 10 MHz.

7. The uterine artery occlusion device of claim 1 wherein said pressure-applying member length comprises a length of between about 0.5 inch and about 5 inches.

8. The uterine artery occlusion device of claim 1 wherein said pressure-applying member length comprises a length of between about 1 inch and about 2 inches.

9. The uterine artery occlusion device of claim 1 wherein said paddle members each have a width between about 0.5 inch and about 2.5 inches.

10. The uterine artery occlusion device of claim 1 wherein said paddle members each have a width of between about 0.7 inch and about 1.3 inches.

11. The uterine artery occlusion device of claim 1 wherein the paddle members have loop-shaped tissue-contacting surfaces.

12. The uterine artery occlusion device of claim 1 wherein paddle members have flat tissue-contacting surfaces.

13. The uterine artery occlusion device of claim 1 wherein the paddle members have curved tissue-contacting surfaces.

14. The uterine artery occlusion device of claim 1 wherein elongated pressure applying members have lengths of between about 3 inches and about 10 inches.

15. The uterine artery occlusion device of claim 1 including an engagement element which is configured to engage a tenaculum to guide the occlusion device to a desired location within a patient's vaginal canal.

16. The uterine artery occlusion device of claim 1 wherein the releasable locking element configured to lock together the paddle bases configured to retain paddle members in a pressure-applying configuration after release thereof from the paddle base looking member.

17. The uterine artery occlusion device of claim 1 wherein said pressure-applying members are configured to apply a pressure of between about 5 pounds per square inch (psi) of pressure and about 80 psi of pressure to tissue disposed between the pressure-applying surfaces of the paddle members.

18. The uterine artery device of claim 17, wherein said pressure applying members are configured to apply a pressure of between about 7 psi and about 10 psi of pressure to tissue disposed between the pressure-applying surfaces of the paddle members.

19. The uterine artery occlusion device of claim 1 wherein each paddle member has a sensor secured to the pressure applying surfaces thereof on distal portions thereof.

20. The uterine artery occluding device of claim 1 wherein the blood flow sensor on the pressure applying surface of one of the paddles has a sensing direction toward the pressure applying surface of the other paddle.

21. The uterine artery occluding device of claim 1 wherein a blood flow sensor disposed on the pressure applying surfaces of both releasable paddles.

22. The uterine artery occluding device of claim 1 wherein the pressure applying paddles are configured to surround an exterior portion of the patient's uterine cervix.

* * * * *